United States Patent [19]
Schülein et al.

[11] Patent Number: 5,792,641
[45] Date of Patent: Aug. 11, 1998

[54] CELLULASE VARIANTS AND DETERGENT COMPOSITIONS CONTAINING CELLULASE VARIANTS

[75] Inventors: Martin Schülein, Copenhagen OE; Henrik Fredholm, Oslo; Carsten Mailand Hjorth, Roskilde; Grethe Rasmussen, Copenhagen NV; Egon Nielsen, Copenhagen; Peter Rosholm, Copenhagen OE, all of Denmark

[73] Assignee: Novo Nordisk A/S, Bagsvaerd, Denmark

[21] Appl. No.: 411,777

[22] PCT Filed: Oct. 6, 1993

[86] PCT No.: PCT/DK93/00327

§ 371 Date: May 5, 1995

§ 102(e) Date: May 5, 1995

[87] PCT Pub. No.: WO94/07998

PCT Pub. Date: Apr. 14, 1994

[30] Foreign Application Priority Data

| Oct. 6, 1992 | [DK] | Denmark | 1221/92 |
| Oct. 6, 1992 | [DK] | Denmark | 1222/92 |
| Oct. 6, 1992 | [DK] | Denmark | 1223/92 |
| Oct. 6, 1992 | [DK] | Denmark | 1224/92 |
| Oct. 6, 1992 | [DK] | Denmark | 1225/92 |
| Dec. 18, 1992 | [DK] | Denmark | 1513/92 |
| Dec. 18, 1992 | [DK] | Denmark | 1515/92 |
| Dec. 23, 1992 | [DK] | Denmark | 1543/92 |

[51] Int. Cl.$^6$ .............. C12N 9/42; C12N 9/00; A61K 38/00; C07K 1/00
[52] U.S. Cl. ............ 435/209; 435/183; 510/114; 530/324; 530/350
[58] Field of Search .............. 435/183, 209; 510/114, 108, 392; 530/324, 350

[56] References Cited

U.S. PATENT DOCUMENTS 4,945,053  7/1990  Ito et al. .............. 435/209

FOREIGN PATENT DOCUMENTS

| 0 468 464 A2 | 7/1991 | European Pat. Off. |
| WO 91/00345 | 1/1991 | WIPO |
| WO 91/10732 | 7/1991 | WIPO |
| WO 91/16423 | 10/1991 | WIPO |
| WO 91/17244 | 11/1994 | WIPO |

OTHER PUBLICATIONS

Chemical Abstracts, vol. 118, p. 358, 1993.

Abstract Japan 3240491.

Russell et al., Nature, vol. 328, pp. 496–500, 1987.

Estell et al., The Journal of Biological Chemistry, vol. 260, No. 11, pp. 6518–6521, 1985.

*Primary Examiner*—Bradley L. Sisson
*Attorney, Agent, or Firm*—Steve T. Zelson, Esq.; Valeta Gregg, Esq.

[57] ABSTRACT

A cellulase variant of a parent cellulase, e.g. a cellulase classified in family 45 such as a *Humicola insolens* 43 kD endoglucanase, comprising a cellulose binding domain (CBD), a catalytically active domain (CAD) and a region linking the cellulose binding domain and catalytically active domain (the linking region), wherein one more amino acid residues of the CBD, CAD or linking region is deleted or substituted by one or more amino acid residues and/or one or more amino acids are added to the linking region and/or another CBD is added at the opposite end of the catalytically active domain, has improved properties as regards e.g. alkaline activity, compatibility with detergent composition ingredients, particulate soil removal, color clarification, defuzzing, depilling, harshness reduction, and sensitivity to anionic surfactants and peroxidase bleaching systems and is useful e.g. in detergent compositions, for textile treatment, in paper pulp processing, for animal feed and for stone washing of jeans.

8 Claims, 11 Drawing Sheets

FIG. 1a

Comparison of 43 kd from fusarium and humicola and pseudomonas

```
                265
Psuegb    VPPIDGGCNG YATRYWDCCK PHCGWSANVP SLVSPLQSCS ANNTRLSDVS
43kdfus             SGSG HSTRYWDCCK PSCSWSGKAA .VNAPALTCD KNDNPISNTN
43kdhum              ADG RSTRYWDCCK PSCGWAKKAP .VNQPVFSCN ANFQRITDFD  42
Homologi  VPPIDG...G .sTRYWDCCK PsCgWs.kap .vn.P..sC. aN..risd..

nr Hum: 43
Psuegb    VGSSCDGGGG .YMCWDKIPF AVSPTLAYGY AATSSGDVCG RCYQLQFTGS
43kdfus   AVNGCEGGGS AYACTNYSPW AVNDELAYGF AATKISGGSE ASWCCACYAL
43kdhum   AKSGCEPGGV AYSCADQTPW AVNDDFALGF AATSIAGSNE AGWCCACYEL  92
Homology  a.sgCegGG. aY.C.d..Pw AVnd.lAyGf AATsi.g..e a.wccacy.l
                                                     119
                                          *           *  * nr Hum: 93
Psuegb    SYNAPGDPGS AALAGKTMIV QATNIGYDVS GGQFDILVPG GGVGAFNACS
43kdfus          TF......TT GPVKGKKMIV QSTNTGGDLG DNHFDLMMPG GGVGIFDGCT
43 kdhum 93      TF......TS GPVAGKKMVV QSTSTGGDLG SNHFDLNIPG GGVGIFDGCT  136
Homology         tf......ts gpvaGkkmIV QsTntGgDlg .nhFDl..PG GGVGIFdgCt Psuegb    AQWGVSNAEL GAQYGGFLAA CKQQLGYNAS LSQYKSCVLN RCDSVFGSRG.
43kdfus        SEFGK..ALG GAQYGGI...    .......    ......SSRS ECDSYPELL..
43kdhum 137   PQFG...GLP GQRYGGI...    .......    ......SSRN ECDRFPDAL.164
Homology  .qfG...al. GaqYGGi...    .......    ......ssrn eCDs.p..l..
```

FIG. 1b

```
                        N172  N178               Q192
                         *     *                  *
Psuegb     LTQLQQGCTW FAEWFEAADN PSLKYKEVPC PAELTTRSGM NRSILNDIRN
43kdfus    ...KDGCHW RFDGCHWFENADN PDFTFEQVQC PKALLDISGC KRDDDSSFPA
43kdhum 165 ...KPGCYW RFDWFKNADN PSFSFRQVQC PAELVARTGC RRNDDGNFPA 209
Homology   ...k.GC.W rfdWFenADN Psf.f.qVqC PaeL..rsGc .R.dd..fpa 245
Psuegb     TCP
43kdfus    FKGDTSASKP QPSSSAKKTT SAAAAAQPQK TKDSAPVVQK SSTKPAAQPE
43kdhum    VQIPSSTSS PVNQPTSTST TSTSTTSSPP VQPTTP....  ........
Homology   ........  .........S .........T .......P.. ........
            251
            SL252

43kdfus    PTKPADKPQT DKPVATHPAA TKPAQPVNKP KTTQKVRGTK TRGSCPAKTD
43kdhum    ........  .........  .........  .........  .........
Homology   ........  .........  .........  .........  .........
                                                              282
                                             280 W             N
                                                 F 43kdfus    ATAKASVVPA YYQCGGSKSA YPNGLACATG SKCVKQNEYY SQCVPN*
43kdhum    ...SGCTAER WAQCGGN..G WSGCTTCVAG STCTKINDWY HQCL*
Homology   .........  QCGG.....  C..G S.C.K.N..Y .QC..N*
CalIj Mutanter i binding: E251S R252L Y280F Y280W Q282N (Y280F, Q282N)
```

FIG. 1b

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

CACCAGCTCT CCGAGCAGCA CGCCTACCAG CACC        3 4

( 2 ) INFORMATION FOR SEQ ID NO:2:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

CGGTTCCCCG ACCCCCTCAA GCC        2 3

( 2 ) INFORMATION FOR SEQ ID NO:3:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

CCAATGTAGC AGTAGAGCAG CCAGCTATGA CCATGATTAC GC        4 2

( 2 ) INFORMATION FOR SEQ ID NO:4:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:4:

CCAATGTAGC AGTAGAGCAG C                 21

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

GTTTTCCCAG TCACGACGTT G                 21

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

AGTGCGATCG ATTCCCCGAC G                 21

( 2 ) INFORMATION FOR SEQ ID NO:7:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

GCCGACAATC CAAGCTTCAG CTT               23

( 2 ) INFORMATION FOR SEQ ID NO:8:

( i ) SEQUENCE CHARACTERISTICS:
        ( A ) LENGTH: 252 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:8:

```
Val Pro Pro Ile Asp Gly Gly Cys Asn Gly Tyr Ala Thr Arg Tyr Trp
 1           5                   10                  15
Asp Cys Cys Lys Pro His Cys Gly Trp Ser Ala Asn Val Pro Ser Leu
            20                  25                  30
Val Ser Pro Leu Gln Ser Cys Ser Ala Asn Asn Thr Arg Leu Ser Asp
        35                  40                  45
Val Ser Val Gly Ser Ser Cys Asp Gly Gly Gly Tyr Met Cys Trp
    50                  55                  60
Asp Lys Ile Pro Phe Ala Val Ser Pro Thr Leu Ala Tyr Gly Ala Ala
65                  70                  75                  80
Ala Thr Ser Ser Gly Asp Val Cys Gly Arg Cys Tyr Gln Leu Gln Phe
```

|  |  |  |  | 85 |  |  |  | 90 |  |  |  | 95 |  |  |
|---|---|---|---|---|---|---|---|---|---|---|---|---|---|---|
| Thr | Gly | Ser | Ser | Tyr | Asn | Ala | Pro | Gly | Asp | Pro | Gly | Ser | Ala | Ala | Leu |
|  |  |  | 100 |  |  |  |  | 105 |  |  |  | 110 |  |  |
| Ala | Gly | Lys | Thr | Met | Ile | Val | Gln | Ala | Thr | Asn | Ile | Gly | Tyr | Asp | Val |
|  |  | 115 |  |  |  |  | 120 |  |  |  |  | 125 |  |  |  |
| Ser | Gly | Gly | Gln | Phe | Asp | Ile | Leu | Val | Pro | Gly | Gly | Gly | Val | Gly | Ala |
|  | 130 |  |  |  |  | 135 |  |  |  |  | 140 |  |  |  |  |
| Phe | Asn | Ala | Cys | Ser | Ala | Gln | Trp | Gly | Val | Ser | Asn | Ala | Glu | Leu | Gly |
| 145 |  |  |  |  | 150 |  |  |  |  | 155 |  |  |  |  | 160 |
| Ala | Gln | Tyr | Gly | Gly | Phe | Leu | Ala | Ala | Cys | Lys | Gln | Gln | Leu | Gly | Tyr |
|  |  |  |  | 165 |  |  |  |  | 170 |  |  |  |  | 175 |  |
| Asn | Ala | Ser | Leu | Ser | Gln | Tyr | Lys | Ser | Cys | Val | Leu | Asn | Arg | Cys | Asp |
|  |  |  | 180 |  |  |  |  | 185 |  |  |  |  | 190 |  |  |
| Ser | Val | Phe | Gly | Ser | Arg | Gly | Leu | Thr | Gln | Leu | Gln | Gln | Gly | Cys | Thr |
|  |  | 195 |  |  |  |  | 200 |  |  |  |  | 205 |  |  |  |
| Trp | Phe | Ala | Glu | Trp | Phe | Glu | Ala | Ala | Asp | Asn | Pro | Ser | Leu | Lys | Tyr |
|  | 210 |  |  |  |  | 215 |  |  |  |  | 220 |  |  |  |  |
| Lys | Glu | Val | Pro | Cys | Pro | Ala | Glu | Leu | Thr | Thr | Arg | Ser | Gly | Met | Asn |
| 225 |  |  |  |  | 230 |  |  |  |  | 235 |  |  |  |  | 240 |
| Arg | Ser | Ile | Leu | Asn | Asp | Ile | Arg | Asn | Thr | Cys | Pro |  |  |  |  |
|  |  |  |  | 245 |  |  |  |  | 250 |  |  |  |  |  |  |

( 2 ) INFORMATION FOR SEQ ID NO:9:

( i ) SEQUENCE CHARACTERISTICS:
    ( A ) LENGTH: 357 amino acids
    ( B ) TYPE: amino acid
    ( C ) STRANDEDNESS: single
    ( D ) TOPOLOGY: linear ( i i ) MOLECULE TYPE: None ( x i ) SEQUENCE DESCRIPTION: SEQ ID NO:9:

| Ser | Gly | Ser | Gly | His | Ser | Thr | Arg | Tyr | Trp | Asp | Cys | Cys | Lys | Pro | Ser |
|---|---|---|---|---|---|---|---|---|---|---|---|---|---|---|---|
| 1 |  |  |  | 5 |  |  |  | 10 |  |  |  |  | 15 |  |  |
| Cys | Ser | Trp | Ser | Gly | Lys | Ala | Ala | Val | Asn | Ala | Pro | Ala | Leu | Thr | Cys |
|  |  |  | 20 |  |  |  |  | 25 |  |  |  |  | 30 |  |  |
| Asp | Lys | Asn | Asp | Asn | Pro | Ile | Ser | Asn | Thr | Asn | Ala | Val | Asn | Gly | Cys |
|  |  | 35 |  |  |  |  | 40 |  |  |  |  | 45 |  |  |  |
| Glu | Gly | Gly | Gly | Ser | Ala | Tyr | Ala | Cys | Thr | Asn | Tyr | Ser | Pro | Trp | Ala |
|  | 50 |  |  |  |  | 55 |  |  |  |  | 60 |  |  |  |  |
| Val | Asn | Asp | Glu | Leu | Ala | Tyr | Gly | Phe | Ala | Ala | Thr | Lys | Ile | Ser | Gly |
| 65 |  |  |  |  | 70 |  |  |  |  | 75 |  |  |  |  | 80 |
| Gly | Ser | Glu | Ala | Ser | Trp | Cys | Cys | Ala | Cys | Tyr | Ala | Leu | Thr | Phe | Thr |
|  |  |  |  | 85 |  |  |  |  | 90 |  |  |  |  | 95 |  |
| Thr | Gly | Pro | Val | Lys | Gly | Lys | Lys | Met | Ile | Val | Gln | Ser | Thr | Asn | Thr |
|  |  |  | 100 |  |  |  |  | 105 |  |  |  |  | 110 |  |  |
| Gly | Gly | Asp | Leu | Gly | Asp | Asn | His | Phe | Asp | Leu | Met | Met | Pro | Gly | Gly |
|  |  | 115 |  |  |  |  | 120 |  |  |  |  | 125 |  |  |  |
| Gly | Val | Gly | Ile | Phe | Asp | Gly | Cys | Thr | Ser | Glu | Phe | Gly | Lys | Ala | Leu |
|  | 130 |  |  |  |  | 135 |  |  |  |  | 140 |  |  |  |  |
| Gly | Gly | Ala | Gln | Tyr | Gly | Gly | Ile | Ser | Ser | Arg | Ser | Glu | Cys | Asp | Ser |
| 145 |  |  |  |  | 150 |  |  |  |  | 155 |  |  |  |  | 160 |
| Tyr | Pro | Glu | Leu | Leu | Lys | Asp | Gly | Cys | His | Trp | Arg | Phe | Asp | Trp | Phe |
|  |  |  |  | 165 |  |  |  |  | 170 |  |  |  |  | 175 |  |
| Glu | Asn | Ala | Asp | Asn | Pro | Asp | Phe | Thr | Phe | Glu | Gln | Val | Gln | Cys | Pro |
|  |  |  | 180 |  |  |  |  | 185 |  |  |  |  | 190 |  |  |

```
Lys Ala Leu Leu Asp Ile Ser Gly Cys Lys Arg Asp Asp Ser Ser
        195                 200             205

Phe Pro Ala Phe Lys Gly Asp Thr Ser Ala Ser Lys Pro Gln Pro Ser
    210                 215                 220

Ser Ser Ala Lys Lys Thr Thr Ser Ala Ala Ala Ala Lys Lys Thr
225                 230             235                 240

Thr Thr Lys Asp Ser Ala Pro Val Val Gln Lys Ser Ser Thr Lys Pro
                245                 250                 255

Ala Ala Gln Pro Glu Pro Thr Lys Pro Ala Asp Lys Pro Gln Thr Asp
        260                 265                 270

Lys Pro Val Ala Thr His Pro Ala Ala Thr Lys Pro Ala Gln Pro Val
        275                 280                 285

Asn Lys Pro Lys Thr Thr Gln Lys Val Arg Gly Thr Lys Thr Arg Gly
    290                 295                 300

Ser Cys Pro Ala Lys Thr Asp Ala Thr Ala Lys Ala Ser Val Val Pro
305                 310                 315                 320

Ala Tyr Tyr Gln Cys Gly Gly Ser Lys Ser Ala Tyr Pro Asn Gly Leu
            325                 330                 335

Ala Cys Ala Thr Gly Ser Lys Cys Val Lys Gln Asn Glu Tyr Tyr Ser
        340                 345                 350

Gln Cys Val Pro Asn
        355
```

( 2 ) INFORMATION FOR SEQ ID NO:10:

( i ) SEQUENCE CHARACTERISTICS:
      ( A ) LENGTH: 284 amino acids
      ( B ) TYPE: amino acid
      ( C ) STRANDEDNESS: single
      ( D ) TOPOLOGY: linear ( i i ) MOLECULE TYPE: None ( x i ) SEQUENCE DESCRIPTION: SEQ ID NO:10:

```
Ala Asp Gly Arg Ser Thr Arg Tyr Trp Asp Cys Cys Lys Pro Ser Cys
1               5               10              15

Gly Trp Ala Lys Lys Ala Pro Val Asn Gln Pro Val Phe Ser Cys Asn
        20              25                  30

Ala Asn Phe Gln Arg Ile Thr Asp Phe Asp Ala Lys Ser Gly Cys Glu
        35              40                  45

Pro Gly Gly Val Ala Tyr Ser Cys Ala Asp Gln Thr Pro Trp Ala Val
    50              55              60

Asn Asp Asp Phe Ala Leu Gly Phe Ala Ala Thr Ser Ile Ala Gly Ser
65              70              75              80

Asn Glu Ala Gly Trp Cys Cys Ala Cys Tyr Glu Leu Thr Phe Thr Ser
            85              90                  95

Gly Pro Val Ala Gly Lys Lys Met Val Val Gln Ser Thr Ser Thr Gly
        100             105                 110

Gly Asp Leu Gly Ser Asn His Phe Asp Leu Asn Ile Pro Gly Gly Gly
        115             120                 125

Val Gly Ile Phe Asp Gly Cys Thr Pro Gln Phe Gly Gly Leu Pro Gly
    130             135                 140

Gln Arg Tyr Gly Gly Ile Ser Ser Arg Asn Glu Cys Asp Arg Phe Pro
145             150                 155                 160

Asp Ala Leu Lys Pro Gly Cys Tyr Trp Arg Phe Asp Trp Phe Lys Asn
                165             170                 175
```

| | | | | | | | | | | | | | | |
|---|---|---|---|---|---|---|---|---|---|---|---|---|---|---|
| Ala | Asp | Asn | Pro 180 | Ser | Phe | Ser | Phe | Arg 185 | Gln | Val | Gln | Cys | Pro 190 | Ala | Glu |
| Leu | Val | Ala 195 | Arg | Thr | Gly | Cys | Arg 200 | Arg | Asn | Asp | Asp | Gly 205 | Asn | Phe | Pro |
| Ala | Val 210 | Gln | Ile | Pro | Ser | Ser 215 | Ser | Thr | Ser | Ser | Pro 220 | Val | Asn | Gln | Pro |
| Thr 225 | Ser | Thr | Ser | Thr | Thr 230 | Ser | Thr | Ser | Thr | Thr 235 | Ser | Ser | Pro | Pro | Val 240 |
| Gln | Pro | Thr | Thr | Pro 245 | Ser | Gly | Cys | Thr | Ala 250 | Glu | Arg | Trp | Ala | Gln 255 | Cys |
| Gly | Gly | Asn | Gly 260 | Trp | Ser | Gly | Cys | Thr 265 | Thr | Cys | Val | Ala | Gly 270 | Ser | Thr |
| Cys | Thr | Lys 275 | Ile | Asn | Asp | Trp | Tyr 280 | His | Gln | Cys | Leu | | | | |

CELLULASE VARIANTS AND DETERGENT COMPOSITIONS CONTAINING CELLULASE VARIANTS

CROSS-REFERENCE TO RELATED APPLICATIONS

This application is a continuation of PCT/DK93/00327 filed Oct. 6, 1993, published as WO94/07998 Apr. 14, 1994, which is incorporated herein by reference and claims priority under § 119 to Danish patent application No. 1221/92, filed 6 Oct. 1992, 1222/92, filed 6 Oct. 1992, 1223/92, filed 6 Oct. 1992, 1224/92, filed 6 Oct. 1992, 1225/92, filed 6 Oct. 1992, 1513/92, filed 18 Dec. 1992, 1515/92, filed 18 Dec. 1992, and 1543/92, filed 23 Dec., 1992, all of which applications are incorporated herein by reference.

1. Field of Invention

The present invention relates to cellulase variants with improved properties.

2. Background of the Invention

Enzymes which are able to degrade cellulose (in the following termed "cellulolytic enzymes" or "cellulases") may be used in paper pulp processing for removing the non-crystalline parts of cellulose, thus increasing the proportion of crystalline cellulose in the pulp, and in animal feed for improving the digestibility of glucans. A further important use of cellulolytic enzymes is for textile treatment, e.g. for reducing the harshness of cotton-containing fabrics (cf., for instance, GB 1 368 599 or U.S. Pat. No. 4,435,307), for soil removal and colour clarification of fabrics (cf., for instance, EP 220 016) or for providing a localized variation in colour to give the fabrics a "stone-washed" appearance (cf., for instance, EP 307 564).

The practical exploitation of cellulolytic enzymes has, to some extent, been set back by the nature of the known cellulase preparations which are often complex mixtures of a variety of single cellulase components, and which may have a rather low specific activity. It is difficult to optimise the production of single components in multiple enzyme systems and thus to implement industrial cost-effective production of cellulolytic enzymes, and their actual use has been hampered by difficulties arising from the need to employ rather large quantities of the enzymes to achieve the desired effect.

The drawbacks of previously suggested cellulolytic enzymes may be remedied by using single-component enzymes selected for a high specific activity. Single-component cellulases are described in, e.g. WO 91/17243, WO 91/17244 and WO 91/10732.

SUMMARY OF THE INVENTION

Further investigations have now shown that improved properties of cellulases may be obtained by one or more specific mutations in the DNA sequence expressing a specific cellulase in order to obtain cellulase variants exhibiting such improved properties.

Accordingly, the present invention relates to a cellulase variant of a parent cellulase comprising a cellulose binding domain (CBD), a catalytically active domain (CAD) and a region linking the cellulose binding domain and catalytically active domain (the linking region), wherein, to improve the properties of the cellulase variant, one or more amino acid residues of the CBD, CAD or linking region is deleted or substituted by one or more amino acid residues and/or one or more amino acids are added to the linking region and/or another CBD is added at the opposite end of the catalytically active domain.

The cellulase variants of the present invention exhibit increased alkaline activity and increased compatibility with other ingredients usually present in detergent compositions such as powder compositions, liquid compositions and heavy duty liquid compositions.

Furthermore, the cellulase variants of the invention, when used in detergent compositions, have improved properties as regards particulate soil removal, colour clarification, defuzzing, depilling and harshness reduction, and they exhibit reduced sensitivity to anionic surfactants and reduced sensitivity to oxidation or the presence of a peroxidase bleaching system.

It is contemplated that the improved properties of the cellulase variants of the invention make the cellulase variants even more useful than the known cellulases e.g. when used in paper pulp processing, in animal feed, for textile treatment and for providing a "stone-washed" appearance of fabrics such as denim, especially of jeans.

The improved properties of the cellulase variants of the invention may be obtained by modifying the parent cellulase either in the linking region or in the CBD or in the CAD or in any combination of these regions and domains as further explained below for the various aspects and embodiments of the invention.

In one aspect of the invention, there is provided a cellulase variant wherein one or more amino acid residues are deleted from the linking region, or wherein one or more amino acids are added to the linking region, or wherein the sensitivity of the cellulase variant towards proteolytic degradation is decreased by deleting, inserting or substituting one or more amino acid residues of said linking region which are sensitive to hydrolysis by proteases by one or more amino acid residues which are resistant to hydrolysis by proteases.

In another aspect of the invention, there is provided a cellulase variant, wherein the binding properties of the cellulase variant are modified by (a) substituting one or more amino acid residues participating in cellulose binding to provide a modified binding affinity, (b) changing the electrostatic charge of the CBD by deleting, inserting or substituting one or more negatively charged amino acid residues of the CBD by neutral or positively charged amino acid residues, or substituting one or more positively charged amino acid residues by positively charged amino acid residues, or substituting one or more positively charged amino acid residues by neutral or negatively charged amino acid residues, or substituting one or more neutral amino acid residues by negatively charged amino acid residues, (c) adding another CBD at the opposite end of the catalytically active domain, (d) substituting one or more amino acid residues by proline.

The object of such modifications is to provide cellulases with a favourable ratio of enzyme performance to tensile strength of cellulase-treated fabric by modifying the binding affinity of the enzyme to the substrate.

In yet another aspect of the invention, there is provided a cellulase variant of a parent cellulase comprising a catalytically active domain (CAD) which comprises an elongated cleft containing the catalytically active site, at least one channel leading from the surface of the cellulase molecule to said cleft, and a positively charged surface region in the vicinity of at least one amino acid residue of the active site and optionally a flexible surface loop region which can close upon the catalytic active site to form a tunnel wherein the substrate is cleaved, wherein, to modify the enzymatic activity, preferably under alkaline conditions, of the cellulase variant, one or more amino acid residues of said cleft, channel or surface region are substituted by one or more other amino acid residues.

In yet another aspect of the invention, there is provided a cellulase variant of a parent cellulase comprising a catalytically active domain (CAD) which comprises an elongated cleft containing the catalytically active site, at least one channel leading from the surface of the cellulase molecule to said cleft, and a positively charged surface region in the vicinity of at least one amino acid residue of the active site, wherein, to reduce the sensitivity of the cellulase variant to anionic surfactants (in particular linear alkyl sulphonates), one or more neutral amino acid residues on the surface of the CAD are substituted by one or more negatively charged amino acid residues, or one or more positively charged amino acid residues on the surface of the CAD are substituted by one or more neutral or negatively charged amino acid residues, or wherein one or more hydrophobic amino acid residues are substituted by one or more non-hydrophobic amino acid residues, or wherein one or more amino acid residues are substituted by proline.

In yet another aspect of the invention, there is provided a cellulase variant of a parent cellulase comprising a CBD, a CAD and a linking region, wherein, to reduce the sensitivity of the cellulase variant to oxidation or to the presence of bleaching agents, one or more amino acid residues on the surface of the CAD, CBD or linking region are substituted by one or more amino acid residues which are less sensitive to oxidation or the presence of a peroxidase bleaching system.

The invention also relates to detergent compositions comprising a cellulase variant of the invention.

THE DRAWINGS

The invention is further illustrated by the drawings, in which

FIGS. 1a and 1b show a sequence alignment of three 43 kD cellulases from *Humicola insolens*, *Fusarium oxysporum* and *Pseudomonas fluorescens*, respectively.

DETAILED DISCLOSURE OF THE INVENTION

Figure 2:
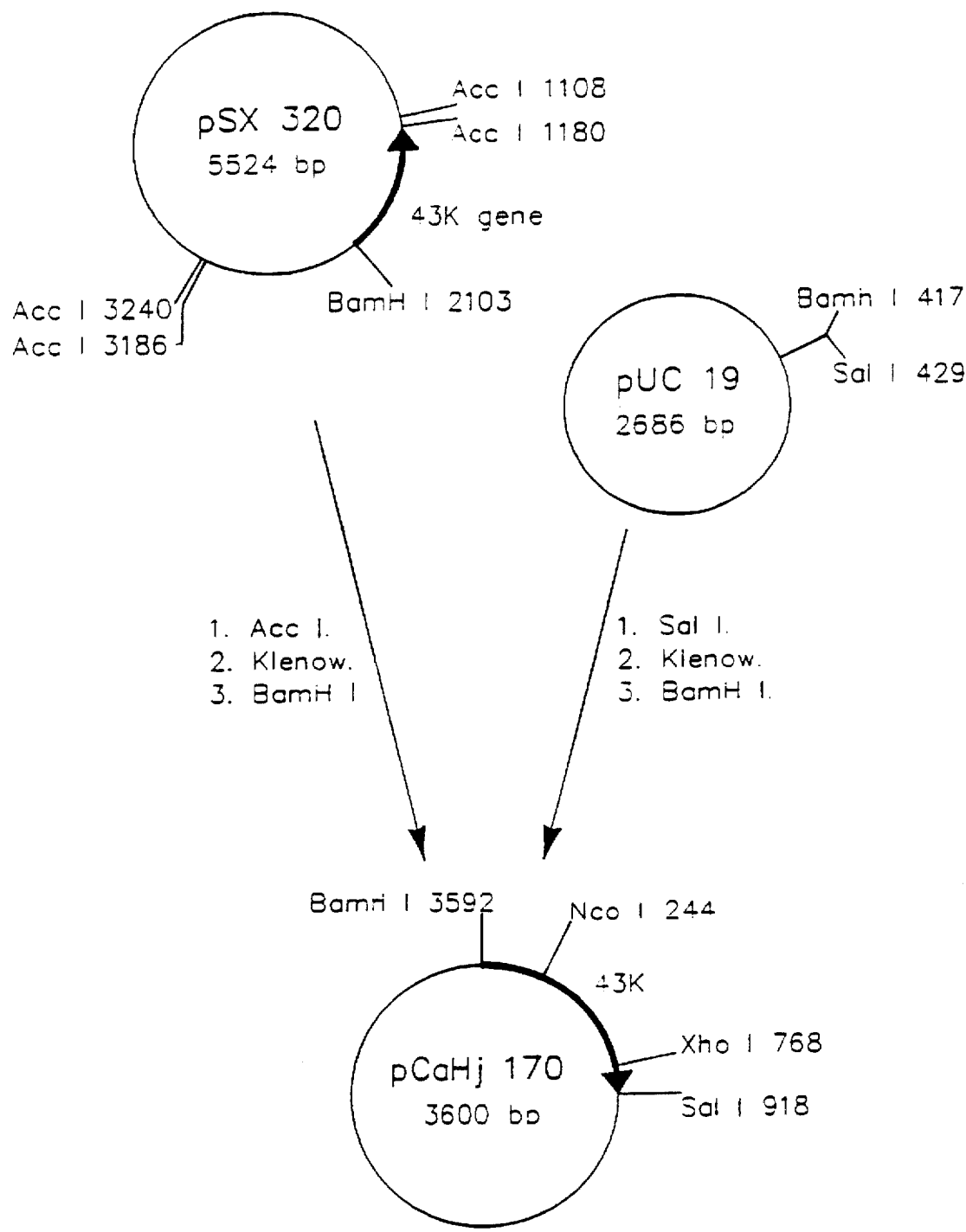
FIG. 2 shows the construction of pCaHj 170.

In the present description and claims, the following abbreviations are used:

| Amino acids: |
|---|
| A = Ala = Alanine |
| V = Val = Valine |
| L = Leu = Leucine |
| I = Ile = Isoleucine |
| P = Pro = Proline |
| F = Phe = Phenylalanine |
| W = Trp = Tryptophan |
| M = Met = Methionine |
| G = Gly = Glycine |
| S = Ser = Serine |
| T = Thr = Threonine |
| C = Cys = Cysteine |
| Y = Tyr = Tyrosine |
| N = Asn = Asparagine |
| Q = Gln = Glutamine |
| D = Asp = Aspartic Acid |
| E = Glu = Glutamic Acid |
| K = Lys = Lysine |
| R = Arg = Arginine |
| H = His = Histidine |

In describing cellulase variants according to the invention, the following nomenclature is used for ease of reference:

original amino acid(s): position(s): substituted amino acid (s)

According to this nomenclature, for instance the substitution of serine for valine in position 221 is shown as:

V221S a deletion of valine in the same position is shown as:

V221* and insertion of an additional amino acid residue such as threonine is shown as:

V221ST

Multiple mutations are separated by pluses, i.e.:

V221S+N222S+Q223T representing mutations in positions 221, 222 and 223 substituting serine and threonine for valine, asparagine and glutamine, respectively.

In the present context, the term "cellulose binding domain" (in the following abbreviated to CBD) is intended to indicate an amino acid sequence (e.g. as described in Kraulis, P., Clore, G. M., Nilges, M., Jones, T. A., Pettersson, G., Knowles, J. and Gronenborn, A. M. Determination of the three-dimensional structure of the C terminal domain of cellobiohydrolase I from Trichoderma Reesel. A study using nuclear magnetic resonance and hybrid distance geometry-dynamical simulated annealing. *Biochemistry* 28:7241–7257, 1989) capable of effecting binding of the cellulase variant to a cellulosic substrate.

The term "catalytically active domain" (in the following abbreviated to CAD) is intended to indicate the core region of the enzyme containing the catalytic site of the enzyme, vide e.g. Gideon et al.: *Nature* (1993) 365, p.362–364.

The term "linking region" is intended to indicate a region adjoining the CBD and connecting it to the CAD of the enzyme. The linking regions identified so far are characterized by being predominantly hydrophillic and uncharged, and by being enriched in certain amino acids to form short, repetitive units imparting flexibility to the sequence. The flexible structure of the linking region is believed to facilitate the action of the catalytically active domain of the enzyme bound to a cellulosic substrate by the CBD. Examples of suitable linking regions are shown in N. R. Gilkes et al., *Microbiol. Rev.* 55, 1991, pp. 303–315).

The term "binding properties" is intended to indicate the affinity with which the CBD binds to a cellulosic substrate, as well as the manner in which the CBD binds under different conditions. For instance the CBD may bind differently at different pH values. This behaviour under different conditions may be modified, e.g. by changing the electrostatic charge of the CBD as indicated above.

The term "another CBD" is intended to include a CBD derived from another cellulase; the additional CBD may be located at the N-terminal end of the catalytically active domain when the "native" CBD is located at the C-terminal end, and vice versa. Substitution by proline specifically is believed to influence the thermal and protease stability of the enzyme.

The parent cellulase is preferably a microbial cellulase. As such, the cellulase may be selected from bacterial cellulases, e.g. Pseudomonas cellulases or Bacillus, such as the Bacillus strains described in U.S. Pat. No. 4,822,516, U.S. Pat. No. 5,045,464 or EP 468 464, or *B. lautus* (cf. WO 91/10732), cellulases. More preferably, the parent cellulases may be a fungal cellulase, in particular Humicola, Trichoderma, Irpex, Aspergillus, Penicillium, Myceliophthora or Fusarium cellulases. Examples of suitable parent cellulases are described in, e.g. WO 91/17244. Examples of suitable Trichoderma cellulases are those described in T. T. Teeri, *Gene* 51, 1987, pp. 43–52. Preferably, the parent cellulase is selected from the cellulases classified in family 45, e.g. the enzymes EG B (*Pseudomonas fluorescens*) and EG V (*Humicola insolens*), as described in Henrissat, B. et al.: *Biochem. J.* (1993), 293, p. 781–788.

A particularly preferred cellulase is one derived from a strain of *Humicola insolens*, such as a *H. insolens* endoglucanase, in particular a *H. insolens* 43 kD endoglucanase as described in WO 91/17243, or a homologue thereof.

In the present context, the term "homologue" is intended to indicate a cellulase the amino acid sequence of which is at least 45% identical to the 43 kD endoglucanase or a cellulase that both adopts the same overall tertiary or three-dimensional (3D) fold as the 43 kD endoglucanase from *H. insolens* and has two acid residues that are involved in catalysis and placed in the active site cleft and optionally an additional acid residue being involved in catalysis and placed in the flexible loop facing the active site cleft.

Sequence comparisons may be performed via known algorithms, such as the one described by Lipman and Pearson, *Science* 227, 1985, p. 1435.

The backbone of a protein can be divided into flexible and structurally conserved regions by means of structural analysis and sequential alignment of homologous proteins. The flexible regions (FR) are the parts of the protein fold where the backbone conformation is likely to change during evolution. The conserved regions (SCR) are the parts of the protein fold where the backbone conformation will be left largely unchanged, i.e. is expected o be conserved in other proteins having the same fold. In addition, SCRs may specify known catalytic or other key residues.

A protein A is defined to have the same overall fold as a protein B if at least one of the following conditions are fulfilled:

1. The 3D structure of A overlap with the SCRs defined for B with an root mean square difference less than 4 Å, preferably less than 3 Å, more preferably less than 2 Å. The root mean square is computed as the Euclidian distance between the residues equivalenced by the SCRs divided by the total number of residue in the SCRs defined for B;

2. The amino acid sequence is compatible with the SCRs defining the fold of B. To measure compatibility, any of the methods for the inverse folding problem described in Wodak, S. J. et al.: *Curr. Opin. Struc. Biol.* 1993, 3, p. 247–259 and the references disclosed therein may be used.

Examples of homologues are the *Pseudomonas fluorescens* cellulase described by H. J. Gilbert et al., op.cit., and the *Fusarium oxysporum* cellulase described in WO 91/17243, vide the attached FIG. 1 showing a sequence alignment of the three cellulases.

In the present context, the term "elongated cleft" refers to a cleft which has dimensions permitting at least three glucose unit of β-1,4-glucan polymeric substrates access to the active site. For improved understanding of the terms used in the present context, reference is made to one specific parent cellulase, the catalytically active domain of which has the overall topology indicated above, i.e. the cellulase described in WO 91/17243 which in the following is referred to as EG V (endoglucanase V). It should, however, be understood that the present invention is in no way intended to be limited to variants of this particular cellulase.

Three crystal structures have been solved for EG V by X-ray crystallography. The three structures describe the native enzyme (Gideon et al.: *Nature* (1993) 365, p.362–364), the native enzyme complexed with cellobiose (Gideon et al.: op.cit.) and the active site mutant D10N complexed with a product consisting of two cellotriose units (Gideon et al., personal communication).

The overall conformation of the enzyme is the same in all three structures with the exception of the flexible surface loop, which is invisible in the native structure, fixed in open position in the structure with cellobiose and in closed position in the structure with cellotriose products.

In EG V, the cleft has a length of about 30 Å, a width of about 9 Å, and a depth of about 7 Å. The dimensions of the cleft are sufficient to permit binding of seven glucose units of β-1,4-glucans. These sites are labelled A, B, C, D, E, F, G, with cleavage occurring between site D and E. In Table 1 below is defined the atoms in EG V that interact with the glucose units at the different sites A–G. Analysis of the cleavage pattern of EG V has shown that binding to sites C–F is necessary for catalysis and that binding to the other sites enhance catalysis. In the structure with cellotriose products, one of the products is bound to sites A–C and the other product is bound to sites E–G with site G being a weak binding site and not very well defined. It is possible to model in a glucose unit at site D with only a few steric overlaps. It is contemplated that the enzyme distorts the normal conformation of glucose unit at position D during catalysis.

When no substrate is bound, the active site cleft is open at the surface to permit docking of a glucan polymer therein. During docking the flexible surface loop region, residue 111–119, changes conformation, with Leu115 moving about 13 Å from a solvent exposed to a buried position, so as to enclose the glucan polymer in a tunnel at the cleavage point between site D and E.

The active site comprises two aspartic acids, Asp10 and Asp121.

Mechanistic studies and the crystal structures supports the theory that EG V is an inverting enzyme with Asp10 functioning as the general base in the catalysis. In addition Asp114 and His119 has been found important for catalysis. Asp114 is involved in binding the glucose unit at site D and together with Ile131 it closes upon the glucose polymer and turns the cleft into a tunnel. It is contemplated that the purpose of the tunnel is to expel water from the environment supply water to Asp10 for the hydrolysis of the glucan polymer. In addition the channel may by used as a means of expelling water from the said cleft during substrate docking.

TABLE 1

| Atom/Residue | Dist | Atom/Water | Dist | Atom/Glucose | Remark |
|---|---|---|---|---|---|
| Site A: | | | | | |
| TRP 18 | | | | | PI-interaction |
| ALA 19:O | 2.90 | HOH 84 | | 2.65 O6A | |
| GLU 48:OE1 | 4.33 | HOH134 | | 3.26 O2A | Possible |
| SER 45:N | 2.78 | HOH 82 | | 4.01 O2A | Possible |
| Site B: | | | | | |
| LYS 21:NZ | 3.05 | | | O3B | |
| LYS 21:NZ | 3.37 | | | O2B | |
| GLU 82:OE1 | 4.08 | | | O5B | Through water |
| TRP 18:NE1 | 2.62 | HOH 79 | | 2.88 O5B | |
| SER 15:OG | 3.83 | | | O2B | Possible |
| SER 45:N | 2.78 | HOH 82 | | 2.94 O6B | |
| Site C: | | | | | |
| PHE132 | | | | | PI-interaction |
| GLY 113:N | 2.80 | HOH 92 | | 2.62 O6C | |
| SER 45:OG | 2.70 | HOH 83 | | 2.75 O6C | |
| | | HOH 92 | | 2.67 O5C | |
| THR111:N | 2.39 | HOH101 | | 3.94 O4C | Possible |
| LYS 13:O | 2.70 | | | O3C | |
| SER110:OG | 2.50 | HOH 77 | | 2.77 O2C | |
| TYR 8:OH | 2.76 | HOH 77 | | | |
| GLU 48:OD1 | 6.92 | | | O3C | Through water |
| Site D: (This site is modelled) | | | | | |
| TYR 8 | | | | | PI-interaction |
| ILE131 | | | | | Steric |
| ASP 10 | 2.71 | HOH103 | | 4.17 C1D | Catalytic |
| ASP121 | | | | | Catalytic |
| VAL129:O | 2.18 (probably further away) | | | O6D | |
| PHE132:N | 3.21 | | | O6D | |
| ASP114:D2 | 4.74 (probably closer) | | | O2D | |
| THR111:O | 2.77 | | | O3D | |
| GLY113:N | 5.32 (probably closer) | | | O3D | |
| Site E: | | | | | |
| TYR147 | | | | | PI-Interaction |
| TYR147:OH | 2.73 | HOH 95 | | 3.11 ASP114:OD1 | Binds loop |
| ASP114:OD1 | 2.48 | | | O6E | |
| GLY128:O | 2.78 | | | O3E | |
| GLY127:O | 2.99 | | | O2E | |
| GLY148:N | 2.92 | | | O2E | |
| Site F: | | | | | |
| ARG 7:N | 3.00 | | | O3F | |
| ASN179:OD1 | 2.35 | | | O6F | |
| Site G: | | | | | |
| ASP178:OD1 | 2.60 | | | O3G | |
| ASP178:OD2 | 2.39 | | | O2G | | around Asp121 and thereby stabilizing the protonated oxygen of Asp121. It has been found that His119 is involved in a hydrogen bond network through Thr6 to the other oxygen of Asp121. This hydrogen bond network may also help stabilizing the protonated form of Asp121. When His119 is positively charged it may, together with other nearby positively charged surface residues, induce a strong electrostatic field over Asp121as the active site is negatively charged. With a glucan polymer bond this field may cause polarization and thereby facilitate cleavage of the bond between the glucose units. A similar electrostatic field is found over the corresponding active acid in lysozyme.

The "channel" leading from the surface to the cleft (in this particular case there are two such channels) is believed to In Table 1, standard PDB notation for naming atoms is used (Bernstein et al. (1977): *InsightII, Biosym Technologies, Inc.*). Reference to hydrogens is made by the heavy they are bounded to, as no hydrogens are present in the structure. The analysis is based on a structure with cellotriose bound at site A–C and E–G. Water molecules present in the structure that participate in binding are referenced explicitly (as HOH). The distances are in Ångstrøm.

In the remarks of Table 1, "PI-interaction" indicates interaction between two aromatic rings; "Through water" indicates cases where no water is present in the structure, but interaction with the substrate may take place through a water molecule; "Possible" indicates atoms that may interact with the substrate in other binding modes; "Steric" indicates no other apparent interaction than that; "Catalytic" indicates catalytic residue.

According to the invention, the cellulase variant is preferably one in which one or more of the amino acids of the linking region are substituted by one or more amino acid residues providing sites for O-glycosylation on expression of the variant in a cell, as it has been found that proteolytic cleavage at O-glycosylated amino acid residues is sterically hindered due to the carbohydrate groups present. In particular, valine, lysine, asparagine or glutamine may be substituted by serine or threonine. Alternatively, one or more amino acid residues of the linking region may be substituted by proline which is resistant to hydrolysis by proteases (including in the presence of detergents).

In this embodiment, one or more amino acid residues are substituted as follows

V221S,T,P

N222S,T,P

Q223S,T,P

V240S,T,P

Q241S,T,P

It may also be advantageous to substitute one or more amino acid residues as follows

V221S+N222S+Q223T

V240S+Q241T

Furthermore, to obtain the desired effect, one or more amino acid residues of the linking region may be deleted, in particular Val, Gln, Lys or Asn, or sequences containing one or more of these amino acids in particular.

The object of such modifications is to provide cellulases with a favourable ratio of enzyme performance to tensile strength of cellulase-treated fabric by modifying the binding affinity of the enzyme to the substrate. To obtain decreased binding of the cellulase variant to a cellulosic substrate, e.g. a fabric, the linking region may be deleted of up to half of its amino acid residues. To obtain increased binding of the cellulase variant to a cellulosic substrate, e.g. a fabric, one or more amino acid residues may be added to the linking region. At least one of these additional amino acid(s) may advantageously be proline.

It should be understood that cellulase variants of the invention may also be obtained by combining a linking region as indicated above with a cellulose binding domain and/or a catalytically active domain derived from another parent cellulase than that providing the linking region.

According to the invention, the cellulase variant is preferably one wherein the binding properties of the cellulase variant are modified by
(a) substituting one or more amino acid residues participating in cellulose binding to provide a modified binding affinity,
(b) changing the electrostatic charge of the CBD by deleting, inserting or substituting one or more negatively charged amino acid residues of the CBD by neutral or positively charged amino acid residues, or substituting one or more positively charged amino acid residues by positively charged amino acid residues, or substituting one or more positively charged amino acid residues by neutral or negatively charged amino acid residues, or substituting one or more neutral amino acid residues by negatively charged amino acid residues,
(c) adding another CBD at the opposite end of the catalytically active domain, or
(d) substituting one or more amino acid residues by proline.

In a preferred embodiment of the invention, one or more amino acid residues of the CBD may be substituted as follows

E251S,Q,N,P

R252L,Q,H

V268E

A269E,R

T265R,E

W253Y,F

A254S,D,G

Q255E,R,K

W261R,Y,F

S262A,N,D

T274R

K275R,Q

I276D,Q,N

N277Q,D

D278P

W279Y,F

Y280W, F

H281S

Q282N,R

Y280F+Q282N.

In the embodiment comprising a cellulase variant to which a CBD has been added at the opposite end of the catalytically active domain, the additional CBD may for instance be derived from one of the cellulases described in WO 91/10732 or WO 91/17244 or Penttila, M. E., Lehtovaara, P., Nevalainen, H., Bhikhabhai, R. and Knowles, J. Homology between cellulase genes of *Trichoderma reesei*: complete nucleotide sequence of the endoglucanase I gene. Gene 45:253–263, 1986; or Saloheimo, M., Lehtovaara, P., Penttila, M. E., Teeri, T. T., Stahlberg, J., Johansson, G., Pettersson, G., Claessens, M. and Tomme, P. EG III, a new endoglucanase from *Trichoderma reesei*. the characterization of both gene and enzyme. Gene 63:11–23, 1988; or Teeri, T. T., Lehtovaara, P., Kauppinen, S., Salovuori, I. and Knowles, J. Homologous domains in *Trichoderma reesei* cellulolytic enzymes: gene sequence and expression of Cellobiohydrolase II. Gene 51:43–52, 1987; or Sims, P., James, C. and Broda, P. The identification, molecular cloning and characterization of a gene from Phanerochaete chrysosporium that shows strong homology to the exocellobiohydrolase i gene from *Trichoderma reesei*. Gene 74:411–422, 1988; or De Oliviera Alzvedo, M. and Radford, A. Sequence of CBH I *Humicola grisea* var. *thermoidea*. Nucleic Acid Research 18:668,1990; or Raguz, S., Yague, E., Wood, D. A. and Thurston, C. F. Isolation and Characterization of a Cellulose-Growth-Specific Gene from Agaricus Bisporus. Gene. 119:183–190, 1992; or Koch, A. and Schulz, G. Cloning, sequencing, and heterologous expression of a cellulase-encoding cdna (CBH1) from penicillium-janthinellum. Gene. 124:57–65, 1993.

According to the invention, the cellulases variant is preferably one wherein, to modify the enzymatic activity of the cellulase variant, one or more amino acid residues of the catalytical active domain (CAD) which comprises an elongated cleft containing the catalytically active site, at least one channel leading from the surface of the cellulase molecule to said cleft and supplying water to said cleft for the hydrolysis of cellulose at the active site, and a positively charged surface region in the vicinity of at least one amino acid residue of, the active site, are deleted or substituted by one or more other amino acids.

In another preferred embodiment, in order to improve the enzymatic activity of the cellulase variant under alkaline conditions, the electrostatic charge in the vicinity of the active site may be changed by substituting one or more positively charged amino acid residues of said cleft by one or more neutral or negatively charged amino acid residues, or by substituting one or more neutral amino acid residues by one or more negatively charged amino acid residues, or by substituting one or more negatively charged amino acid residues by more negatively charged amino acid residue(s).

In yet another preferred embodiment, the cellulase variant may be one in which the catalytically active domain is additionally provided with a flexible surface loop region. To improve the enzymatic activity of the cellulase variant under alkaline conditions, one or more amino acid residues of said loop region or one or more amino acids involved in hydrogen bond network to an amino acid residue of the active site are substituted by one or more amino acid residues so as to modify said hydrogen bond network.

The enzymatic activity of the cellulase variant under alkaline conditions may also be improved by substituting one or more amino acid residues of the flexible loop region by one or more amino acid residues so as to change to flexibility of the loop, i.e. by preserving the ability of the loop to participate in a hydrogen bond network to an amino acid residue of the active site.

Also, in order to improve the enzymatic activity of the cellulase variant under alkaline conditions, one or more amino acid residues of the surface of the active site cleft may be substituted by one or more amino acid residues so as to modify the capability of the surface to interact with a substrate.

Furthermore, the enzymatic activity of the cellulase variant under alkaline conditions may be improved by substituting one or more amino acid residues of the surface of the channel leading to the active site cleft by one or more amino acid residues so as modify the flow of water through the channel.

In a further preferred embodiment, the cellulase variant is one wherein, to improve the enzymatic activity of the cellulase variant under alkaline conditions, one or more neutral or negatively charged amino acid residues of the positively charged surface region are substituted by one or more positively charged amino acid residues to increase the positive net charge of the region.

Regions I–X shown below correspond to the following positions in the 43 kD endoglucanase sequence:

| Region | Residues |
| --- | --- |
| I | 2–21 |
| II | 44–48 |
| III | 55–60 |
| IV | 65–67 |
| V | 72–75 |
| VI | 95–103 |
| VII | 109–123 |
| VIII | 128–136 |
| IX | 142–148 |
| X | 175–185 |

In one embodiment of a variant *H. insolens* 43 kD endoglucanase or a homologous cellulase, the surface conformation of said cleft, channel(s) and/or loop may be modified by substituting one or more amino acid residues in one or more of the regions I–VII or IX–X shown above or in one or more of positions 28, 37 or 90.

More specifically, the surface conformation of said cleft may be changed by substituting one or more amino acid residues in one or more of the positions 4, 5, 6, 7, 8, 10, 11, 12, 13, 15, 18, 20, 21, 44, 45, 48, 74, 110, 114, 117, 119, 121, 128, 131, 132, 147, 176, 178 or 179 of the 43 kD endoglucanase. It is anticipated that amino acid residues in corresponding positions of homologous cellulases may likewise be substituted.

In another embodiment, the surface conformation and/or the hydrogen bonding properties of the loop region may be changed by substituting one or more amino acid residues in region VII shown above. More specifically, the surface conformation of said loop region may be changed by substituting one or more amino acid residues in one or more of the positions 111, 112, 113, 114, 115, 116, 117, 118 or 119. It is anticipated that amino acid residues in corresponding positions of homologous cellulases may likewise be substituted.

In a further embodiment, the surface conformation of said channel(s) may be changed by substituting one or more amino acid residues in one or more of the regions I, III, V or VII–IX. More specifically, the surface conformation of said channel(s) may be changed by substituting one or more amino acid residues at one or more of the positions 9, 14, 28, 37, 55, 58, 59, 60, 63, 72, 78, 109, 118, 123, 129, 131, 132, 133, 136, 142, 145, 146, 158, 163, 176, 179, 186 or 196. It is anticipated that amino acid residues in corresponding positions of homologous cellulases may likewise be substituted.

In a still further embodiment, the positive electrostatic charge of the positively charged surface region may be changed by substituting one or more amino acid residues in one or more of the regions IV, VI or X, or in position 2. More specifically, the positive electrostatic charge may be changed by substituting one or more amino acid residues in one or more of the positions 2, 13, 20, 44, 65, 66, 67, 90, 95, 96, 97, 98, 100, 102, 103, 175, 176, 178, 179, 180, 183 or 185. It is anticipated that amino acid residues in corresponding positions of homologous cellulases may like-wise be substituted.

In a still further embodiment, the negative electrostatic charge of said cleft may be changed by substituting one or more amino acid residues in one or more of the positions 55, 74, 90 or 123. It is anticipated that amino acid residues in corresponding positions of homologous cellulases may likewise be substituted.

More specifically, one or more amino acid residues may be substituted as follows:
D2N
S5A
T6S
Y8F
W9S,G
D10E
K13R
S15N,A,D
W18H
K20R
V28T
R37N,S,A
K44R
S45N,D
E48D,Q,A
S55E,D
D58N,S,A
Q59S,A,G
N65R
D66R,N D67R,N
A74S,D,N
Y90F
S96R
A100R
K102R
K103R
S110N,A,D
T111G,A,S
G112A
G113A
L115I,V,F,H,T,N,Q,G
G116A
S117G,A,D,E,N,Q
N118G,A,S,D,R
H119Q,K
N123D,E,Y
K175R
N179D,H,A
S185R,K
C11A+C135A
C12A+C47A
R37N+D58A The present invention also relates to a cellulase variant wherein, to reduce the sensitivity of the cellulase variant to anionic surfactants, one or more neutral amino acid residues on the surface of the CAD are substituted by one or more negatively charged amino acid residues, or one or ore positively charged amino acid residues on the surface of the CAD are substituted by one or more neutral or negatively charged amino acid residues, or wherein one or more hydrophobic amino acid residues are substituted by one or more non-hydrophobic amino acid residues, or wherein one or more amino acid residues are substituted by proline, the CAD comprising an elongated cleft containing the catalytically active site, least one channel leading from the surface of the cellulase molecule to said cleft and supplying water to said cleft for the hydrolysis of cellulose at the active site, and a positively charged surface region in the vicinity of at least one amino acid residue of the active site.

It has been found that the presence of anionic surfactants (in particular linear alkyl sulphonate) may inhibit the activity of the cellulase. It is currently believed that such inhibition is caused by the negatively charged head of the surfactant binding to positively charged amino acid residues on the surface of the cellulase molecule and the hydrophobic tail of the surfactant binding to hydrophobic amino acid residues on the surface of the cellulase molecule. This binding pattern is believed to result in local unfolding of the protein and consequently loss of activity. As indicated above, inhibition of the cellulase by anionic surfactants may be remedied by substituting negatively charged amino acid residues for neutral or positively charged residues on the protein surface or by substituting hydrophobic amino acid residues at the protein surface with hydrophillic residues. It is, however, currently believed to be less appropriate to substitute positively charged amino acid residues in the surface region in the vicinity of at least one amino acid residue of the active site, as this might have an adverse effect on the electrostatic potential of the CAD. Furthermore, it has been found that substitution by proline may stabilise the enzyme by increasing the rigidity of the backbone.

In one embodiment of a variant *H. insolens* 43 kD endoglucanase or a homologous cellulase, it is expected that the surface conformation of said protein surface may be modified by substituting one or more amino acid residues in one or more of the regions VIII–X shown above or a region corresponding thereto in a homologous cellulase, or in positions 37, 62, 63, 78, 118, 158, 163, 179, 186 or 196.

In this embodiment, one or more amino acid residues may be substituted in one or more of the positions 37, 62, 63, 78, 118, 129, 131, 133, 136, 142, 146, 158, 163, 175, 176, 179, 186 or 196.

More specifically, one or more amino acid residues may be substituted as follows
R37N,S,A
W62E,F
A63D,T,R
A78D
N118D
V129D,T,S
I131L,V,T,N,Q,H,G
D133Q
T136D
L142D,T,S
R146E,Q,S
R158D
L163N
N176D
N179D
N186D
R196D.

Alternatively, one or more amino acids may be substituted as follows
A78P
A162P
K175G,S The present invention also relates to a cellulase variant wherein, to reduce the sensitivity of the cellulase variant to oxidation or to the presence of bleaching agents, one or more amino acid residues on the surface of the CAD, CBD or linking region are substituted by one or more amino acid residues which are less sensitive to oxidation or the presence of a peroxidase bleaching system; the CAD comprising an elongated cleft containing the catalytically active site, at least one channel leading from the surface of the cellulase molecule to said cleft and supplying water to said cleft for the hydrolysis of cellulose at the active site, and a positively charged surface region in the vicinity of at least one amino acid residue of the active site.

According to the invention, it has been found that certain amino acids, e.g. methionine, are sensitive to oxidation e.g. by hypochlorite, while others, e.g. tryptophan or tyrosine are sensitive to the presence of bleaching agents such as peroxidase systems, resulting in inactivation of the enzyme. In the present context, the term "peroxidase system" is intended to indicate a bleaching system comprising a peroxidase, a substrate for the peroxidase and a bleach accelerator, e.g. as described in WO 89/09813 or Wo 91/05839. It has furthermore been found that this problem may be alleviated by appropriate substitutions by less sensitive amino acid residues, e.g. serine, asparagine, glutamine, proline, phenylalanine, glutamic acid, or glycine.

In one embodiment of a variant *H. insolens* 43 kD endoglucanase or a homologous cellulase, it is expected that the surface conformation of the enzyme may be modified by substituting one or more amino acid residues in one or more of the regions IX or X shown above or in one or more of positions 62 or 104.

In one embodiment of a variant *H. insolens* 43 kD endoglucanase, one or more amino acid residues may be substituted in one or more of the positions 8, 9, 18, 62, 104, 147 or 175.

More specifically, one or more amino acid residues are substituted as follows

Y8F
W9F,H,S,A
W18H,F,A
W62F,E
M104S,N,Q
Y147F,H,S,Q,N,E,D.

Methods of preparing cellulase variants of the invention

Several methods for introducing mutations into genes are known in the art. After a brief discussion of cloning cellulase-encoding DNA sequences, methods for generating mutations at specific sites within the cellulase-encoding sequence will be discussed.

Cloning a DNA sequence encoding a cellulase

The DNA sequence encoding a parent cellullose may be isolated from any cell or microorganism producing the cellulase in question by various methods, well known in the art. First a genomic DNA and/or cDNA library should be constructed using chromosomal DNA or messenger RNA from the organism that produces the cellulase to be studied. Then, if the amino acid sequence of the cellulase is known, homologous, labelled oligonucleotide probes may be synthesized and used to identify cellulase-encoding clones from a genomic library of bacterial DNA, or from a fungal CDNA library. Alternatively, a labelled oligonucleotide probe containing sequences homologous to cellulase from another strain of bacteria or fungus could be used as a probe to identify cellulase-encoding clones, using hybridization and washing conditions of lower stringency.

Yet another method for identifying cellulase-producing clones would involve inserting fragments of genomic DNA into an expression vector, such as a plasmid, transforming cellulase-negative bacteria with the resulting genomic DNA library, and then plating the transformed bacteria onto agar containing a substrate for cellulase. Those bacteria containing cellulase-bearing plasmid will produce colonies surrounded by a halo of clear agar, due to digestion of the substrate by secreted cellulase.

Alternatively, the DNA sequence encoding the enzyme may be prepared synthetically by established standard methods, e.g. the phosphoamidite method described by S. L. Beaucage and M. H. Caruthers, Tetrahedron Letters 22, 1981, pp. 1859–1869, or the method described by Matthes et al., The EMBO J. 3, 1984, pp. 801–805. According to the phosphoamidite method, oligonucleotides are synthesized, e.g. in an automatic DNA synthesizer, purified, annealed, ligated and cloned in appropriate vectors.

Finally, the DNA sequence may be of mixed genomic and synthetic, mixed synthetic and cDNA or mixed genomic and cDNA origin prepared by ligating fragments of synthetic, genomic or cDNA origin (as appropriate), the fragments corresponding to various parts of the entire DNA sequence, in accordance with standard techniques. The DNA sequence may also be prepared by polymerase chain reaction (PCR) using specific primers, for instance as described in US 4,683,202 or R. K. Saiki et al., Science 239, 1988, pp. 487–491.

Site-directed mutagenesis of the cellulase-encoding sequence

Once a cellulase-encoding DNA sequence has been isolated, and desirable sites for mutation identified, mutations may be introduced using synthetic oligonucleotides. These oligonucleotides contain nucleotide sequences flanking the desired mutation sites; mutant nucleotides are inserted during oligonucleotide synthesis. In a specific method, a single-stranded gap of DNA, bridging the cellulase-encoding sequence, is created in a vector carrying the cellulase gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al., (1984, Biotechnology 2:646–639). U.S. Pat. No. 4,760,025, by Estell et al., issued Jul. 26, 1988, discloses the introduction of oligonucleotides encoding multiple mutations by performing minor alterations of the cassette, however, an even greater variety of mutations can be introduced at any one time by the Morinaga method, because a multitude of oligonucleotides, of various lengths, can be introduced.

Another method of introducing mutations into cellulase-encoding sequences is described in Nelson and Long, Analytical Biochemistry 180, 1989, pp. 147–151. It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Construction of a system for site directed mutagenesis of Carezyme (43 kD cellulase from H. insolens)

A plasmid (pSX 320) enabling expression of the Humicola insolens ~43 kD endoglucanase (karyosome) in Aspergillus oryzae has been described in an earlier patent (PCT/DK 91/00123). The gene encoding karyosome was subcloned from pSX 320 into pUC 19 (C. Yanisch-Perron et. al.(1985). Gene 33, 103–119) as described in FIG. 2.

A Cla I restriction site was introduced into pCaHj 170 in the 43K gene as a silent site directed mutation in position 537.

Figure 4:
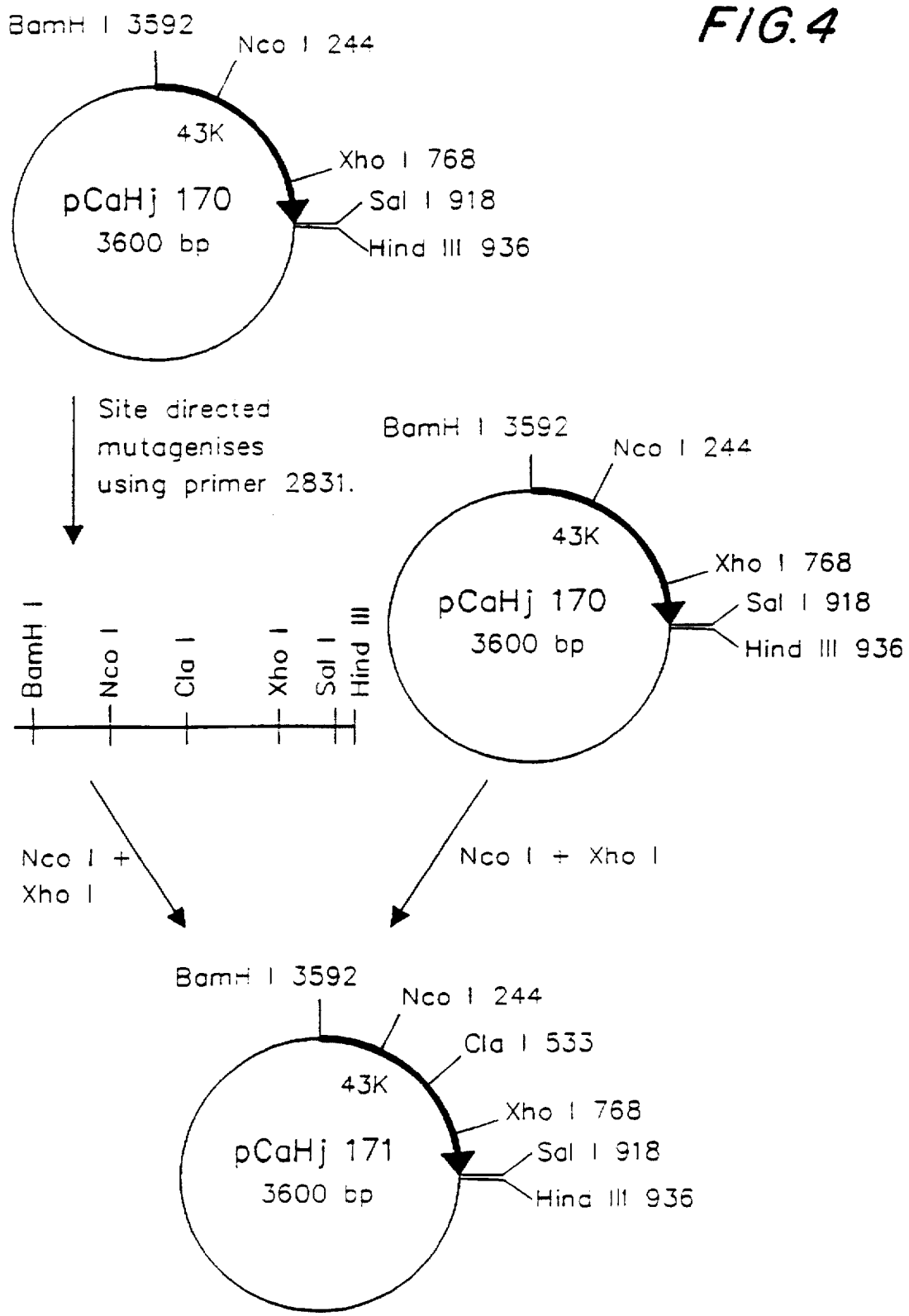
FIG. 4 shows the construction of pcaHj 171.
Figure 5:
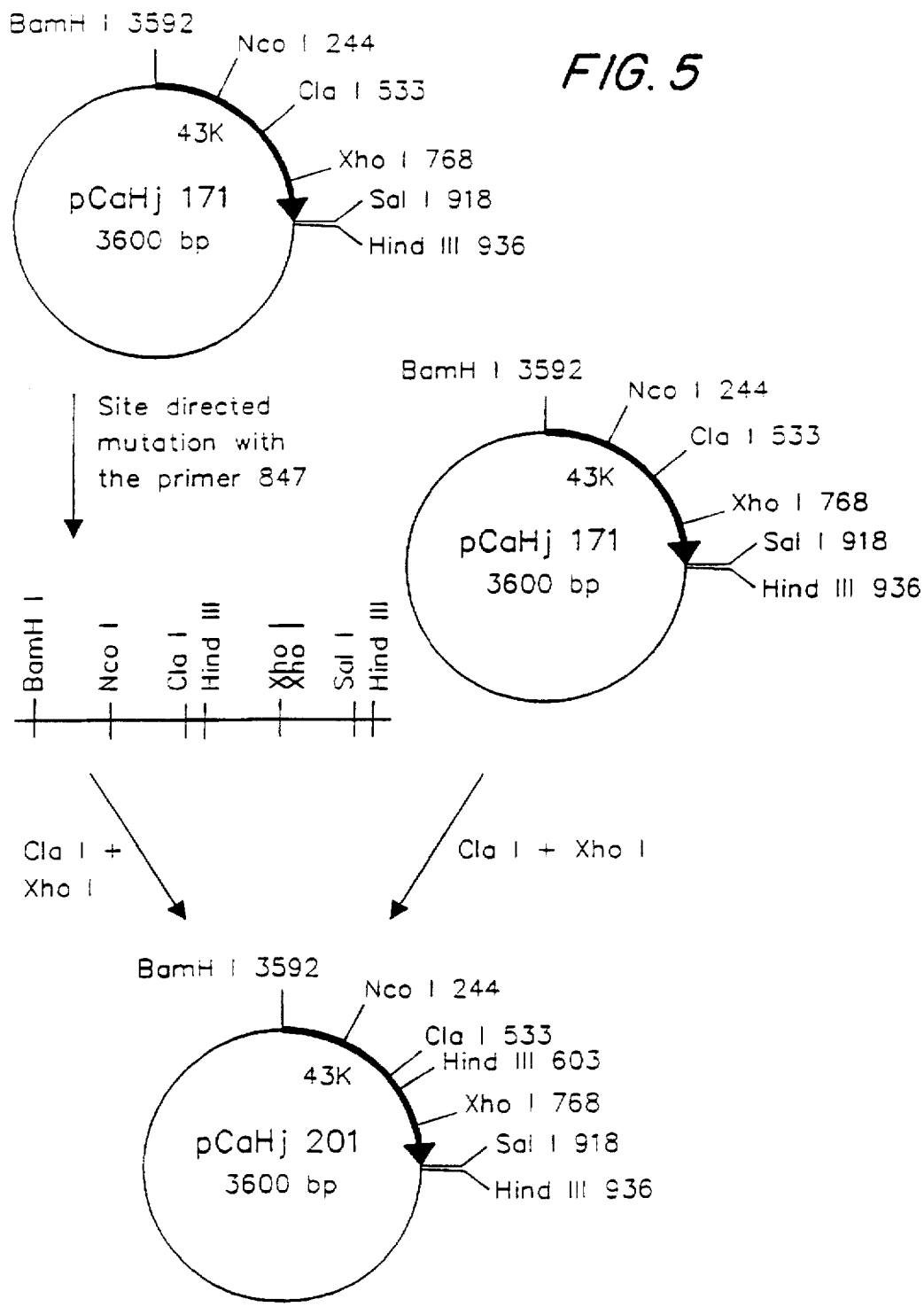
FIG. 5 shows the construction of pCaHj 201.

Site directed mutagenesis was done using the PCR method of Nelson and Long (R. M. Nelson, G. L. Long. (1989). Anal. Biochem. 180, 147–151). The details is given in FIG. 3. The plasmids pCaHj 171 and pCaHj 201 was constructed from pCaHj 170 as shown in FIGS. 4 and 5.

Figure 6:
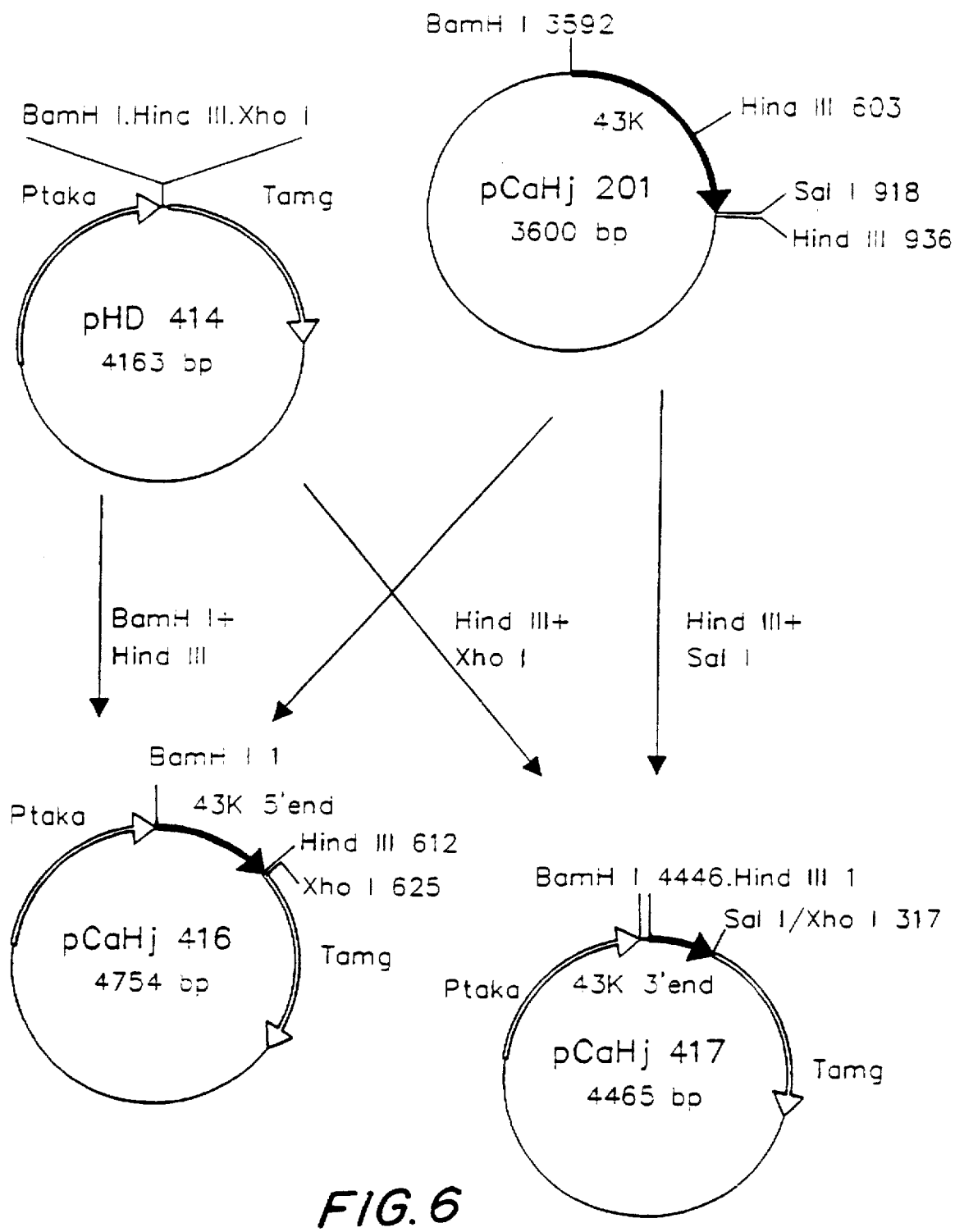
FIG. 6 shows the construction of pCaHj 416 and pCaHj 417.
Figure 7:
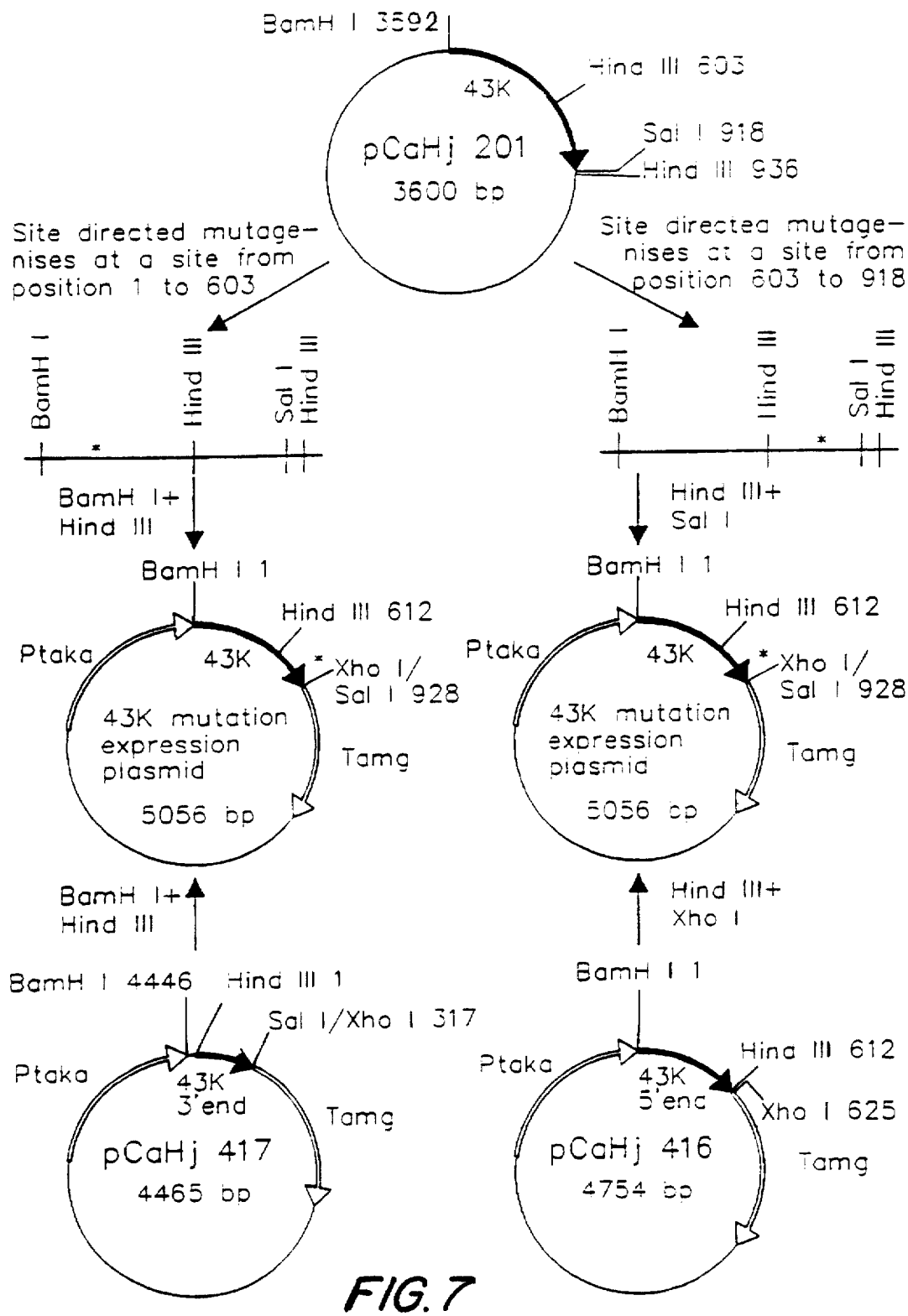
FIG. 7 shows the construction of mutants using pCaHj 201 as template.

Two plasmids, pCaHj 416 and pCaHj 417, enabling the use of pCaHj 201 for mutant construction were made from the Aspergillus expression plasmid pHD 414 .The construction of these plasmids are summarised in FIG. 6.

pCaHj 201 was used for construction of mutants as shown in FIG. 7.

The expression plasmids harbouring the mutated 43K genes were transformed into Aspergillus oryzae IFO 4177 using selection on acetamide by cotransformation with pToC 90 as described in the patent application(PCT/DK/00123).

Construction of the mutants CC234 and CC248

The mutant CC234, consisting of V221S, cN222S, Q223T was constructed using the oligonucleotide 4214.

4214 5' CACCAGCTCTCCGAGCAGCACGCCTACCAGCACC
3'  (SEQ ID No:1)

The mutations were introduced as described in FIG. 6, subcloning the mutated Hind III—Sal I fragment into pCaHj 416.

The mutant CC248, consisting of A162P was constructed using the oligonucleotide 4271.

4271 5' CGGTTCCCCGACCCCCTCAAGCC 3'  (SEQ ID No:2).

The mutation was introduced as described in FIG. 6, subcloning the mutated BamH I—Hind III fragment into pCaHj 417.

In the following, the attached FIGS. 2–7are explained further:

FIG. 2. construction of pcaHj 170 pSX 320 was digested with Acc I. The digestion was terminated by phenol/chloroform extraction, precipitation with ethanol and drying in vacuo. Recessed 3' ends were filled in using the Klenow polymerase and the reaction was terminated as described above. The DNA was redissolved and digested with BamH I. The 920 bp fragment containing the karyosome gene was isolated from an agarose gel. pUC 19 was digested with Sal I, recessed 3' ends filled in with the Klenow polymerase and the DNA was then digested with BamH I as described above. The formed 2675 bp fragment was isolated from an agarose gel.

The 920 bp pSX 320 fragment was ligated to the 2675 bp pUC 19 fragment and transformed into E. coli MT 172, an E. coli MC 1000 strain (Casadaban and Cohen (1980). J. Mol. Biol., 138, 179–207) made r–m+by conventional methods. The resulting plasmid was termed pCaHj 170.

Figure 3:
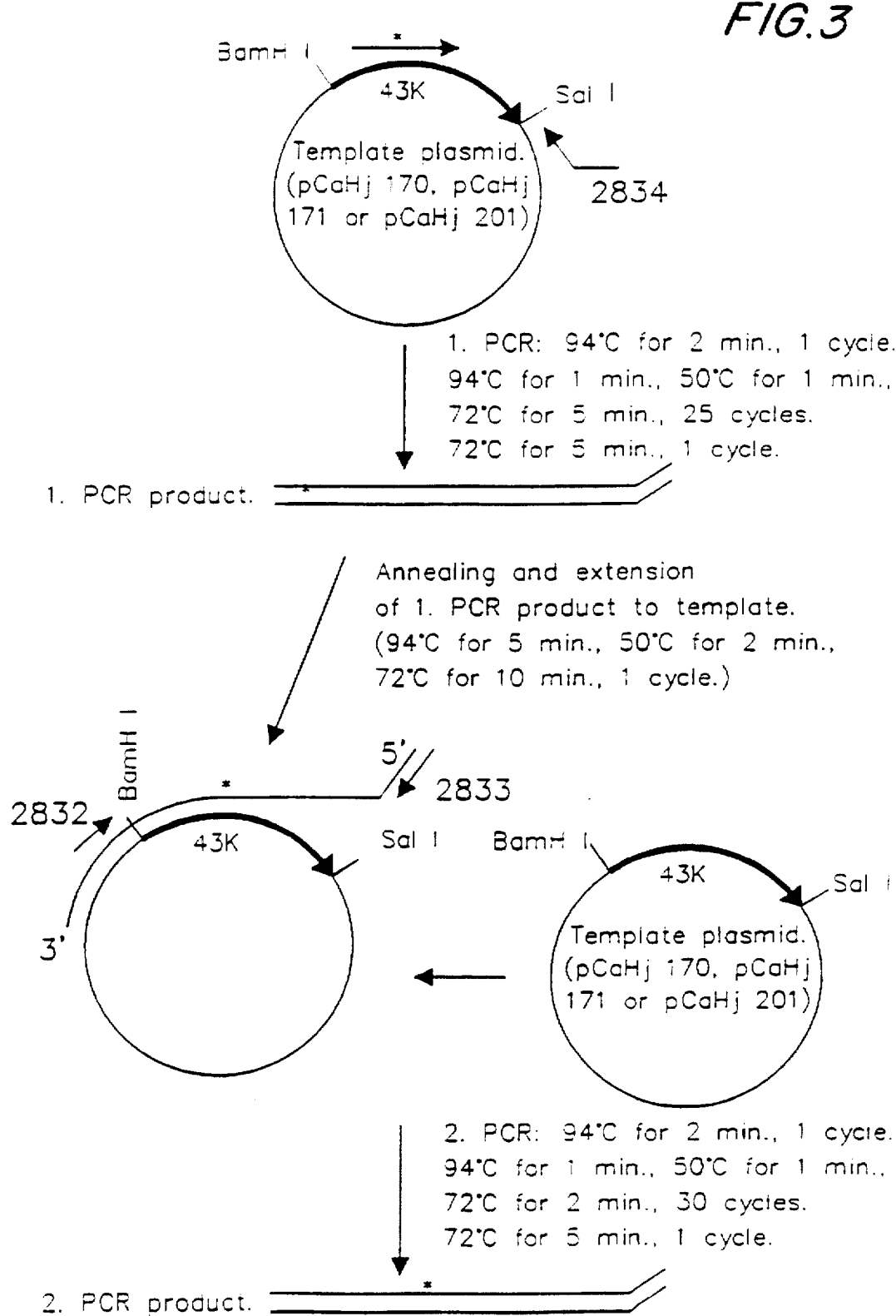
FIG. 3 shows the site directed mutagenesis of the 43K gene.

FIG. 3. site directed mutagenesis of the 43K gene

The plasmids pcaHj 170, pCaHj 171 or pCaHj 201 were used as templates dependant on the mutation in question. The template of choice was amplified using a mutagenic primer (shown as arrow with asterisk) and the primer 2834, a 42 nucleotides primer matching the template in the 3' end (21 nucleotides) and mismatching the template in the 5' end (21 nucleotides.):

2834: 5'CCAATGTAGCAGTAGAGCAGCCAGCTAT-
GACCATGATTACGC 3' (SEQ ID No:3 )

The temperature cycling profile was as indicated on the figure using taq polymerase from Perkin-Elmer Cetus (amplitaq™) following the manufacturers instructions.

The 1. PCR product was isolated from an agarose gel and extended in a PCR cycler using the same template as above. The temperature profile was as indicated on the figure using amplitaq™ and standard PCR conditions. After the extension the PCR primers 2833 and 2832 was added directly to the extension mixture, and the temperature cycling programme indicated on the figure was run, and the resulting PCR fragment harbouring the mutation was isolated from an agarose gel.

The PCR primer 2833 corresponded to the 5' end of 2834:

2833: 5' CCAATGTAGCAGTAGAGCAGC 3' (SEQ ID No:4)

The primer 2832 corresponds to the template:

2832: 5' GTTTTCCCAGTCACGACGTTG 3' (SEQ ID No:5).

FIG. 4. construction of pCaHj 171

A silent mutation in the 43K gene (G to A in the third position of an Arg codon) was introduced into the 43K gene using pCaHj 170 as a template and the mutagenic primer 2831:

2831: 5' AGTGCGATCGATTCCCCGACG 3' (SEQ ID No:6).

The mutated PCR fragment was digested with Nco I and Xho I and ligated to pCaHj 170 digested with Nco I and Xho I. The ligation mixture was transformed into E. coli MT 172. The Nco I-Xho I insert was sequenced from a recombinant plasmid using the Sequenase™ kit from United States Biochemicals following the manufacturers instructions. The sequence was identical to the sequence of pCaHj 170 except for the desired mutation. This plasmid was termed pCaHj 171.

FIG. 5. construction of pCaHj 201

A silent mutation in the 43K gene (G to A in the third position of a Pro codon) was introduced into the 43K gene using pCaHj 171 as a template and the mutagenic primer 847:

847: 5' GCCGACAATCCAAGCTTCAGCTT 3' (SEQ ID No:7).

The mutated PCR fragment was digested with Cla I and Xho I and ligated to pCaHj 171 digested with Cla I and Xho I. The ligation mixture was transformed into E. coli MT 172. The Cla I-Xho I insert was sequenced from a recombinant plasmid using the Sequenase™ kit from United States Biochemicals following the manufacturers instructions. The sequence was identical to the sequence of pCaHj 171 except for the desired mutation. This plasmid was termed pCaHj 201.

FIG. 6. construction of pCaHj 416 and pCaHj 417

Construction of pCaHj 416: pCaHj 201 was digested with BamH I and Hind III, and the 612 bp fragment was ligated into pHD 414 digested with BamH I and Hind III.

Construction of pCaHj 417: pCaHj 201 was digested with Hind III and Sal I, and the 317 bp fragment was ligated into pHD 414 digested with Hind III and Xho I.

FIG. 7. construction of mutants using pCaHj 201 as template

The site directed mutagenesis was performed as described in FIG. 2. When the alterations were located upstream the Hind III site (pos. 1–612) the mutated PCR fragment was digested with BamH I and Hind III, and the generated 612 bp fragment was ligated to pCaHj 417 digested with BamH I and Hind III resulting in an expression plasmid for the mutated gene.

When the alterations were located downstream the Hind III site (pos. 612–928) the mutated PCR fragment was digested with Hind III and Sal I, and the generated 316 bp fragment was ligated to pCaHj 416 digested with hind II and Xho I resulting in an expression plasmid for the mutated gene. The plasmid sizes and restriction site positions corresponds to substitutions only. In case of deletions or insertions size and site positions are different from the shown figures.

Expression of cellulase variants

According to the invention, a mutated cellulase-coding sequence produced by methods described above, or any alternative methods known in the art, can be expressed, in enzyme form, using an expression vector which typically includes control sequences encoding a promoter, operator, ribosome binding site, translation initiation signal, and, optionally, a repressor gene or various activator genes. To permit the secretion of the expressed protein, nucleotides encoding a "signal sequence" may be inserted prior to the cellulase-coding sequence. For expression under the direction of control sequences, a target gene to be treated according to the invention is operably linked to the control sequences in the proper reading frame. Promoter sequences that can be incorporated into plasmid vectors, and which can support the transcription of the mutant cellulase gene, include but are not limited to the prokaryotic β-lactamase promoter (Villa-Kamaroff, et al., 1978, Proc. Natl. Acad. Sci. U.S.A. 75:3727–3731) and the tac promoter (DeBoer, et al., 1983, Proc. Natl. Acad. Sci. U.S.A. 80:21–25). Further references can also be found in "Useful proteins from recombinant bacteria" in Scientific American, 1980, 242:74–94.

According to one embodiment B. subtilis is transformed by an expression vector carrying the mutated DNA. If expression is to take place in a secreting microorganism such as B. subtilis a signal sequence may follow the translation initiation signal and precede the DNA sequence of interest. The signal sequence acts to transport the expression product to the cell wall where it is cleaved from the product upon secretion. The term "control sequences" as defined above is intended to include a signal sequence, when is present.

In a currently preferred method of producing cellulase variants of the invention, a filamentous fungus is used as the host organism. The filamentous fungus host organism may conveniently be one which has previously been used as a host for producing recombinant proteins, e.g. a strain of Asperaillus sp., such as *A. niger*, *A. nidulans* or *A. oryzae*. The use of *A. oryzae* in the production of recombinant proteins is extensively described in, e.g. EP 238 023.

For expression of cellulase variants in Asperaillus, the DNA sequence coding for the cellulase variant is preceded by a promoter. The promoter may be any DNA sequence exhibiting a strong transcriptional activity in Aspergillus and may be derived from a gene encoding an extracellular or intracellular protein such as an amylase, a glucoamylase, a protease, a lipase, a cellulase or a glycolytic enzyme.

Examples of suitable promoters are those derived from the gene encoding *A. oryzae* TAKA amylase, *Rhizomucor miehei* aspartic proteinase, *A. niger* neutral a-amylase, *A. niger* acid stable α-amylase, *A. niger* glucoamylase, *Rhizomucor miehei* lipase, *A. oryzae* alkaline protease or *A. oryzae* triose phosphate isomerase.

In particular when the host organism is *A. oryzae*, a preferred promoter for use in the process of the present invention is the *A. oryzae* TAKA amylase promoter as it exhibits a strong transcriptional activity in *A. oryzae*. The sequence of the TAKA amylase promoter appears from EP 238 023.

Termination and polyadenylation sequences may suitably be derived from the same sources as the promoter.

The techniques used to transform a fungal host cell may suitably be as described in EP 238 023.

To ensure secretion of the cellulase variant from the host cell, the DNA sequence encoding the cellulase variant may be preceded by a signal sequence which may be a naturally occurring signal sequence or a functional part thereof or a synthetic sequence providing secretion of the protein from the cell. In particular, the signal sequence may be derived from a gene encoding an Aspergillus sp. amylase or glucoamylase, a gene encoding a *Rhizomucor miehei* lipase or protease, or a gene encoding a Humicola cellulase, xylanase or lipase. The signal sequence is preferably derived from the gene encoding *A. oryzae* TAKA amylase, *A. niger* neutral α-amylase, *A. niger* acid-stable α-amylase or *A. niger* glucoamylase.

The medium used to culture the transformed host cells may be any conventional medium suitable for growing Aspergillus cells. The transformants are usually stable and may be cultured in the absence of selection pressure. However, if the transformants are found to be unstable, a selection marker introduced into the cells may be used for selection.

The mature cellulase protein secreted from the host cells may conveniently be recovered from the culture medium by well-known procedures including separating the cells from the medium by centrifugation or filtration, and precipitating proteinaceous components of the medium by means of a salt such as ammonium sulphate, followed by chromatographic procedures such as ion exchange chromatography, affinity chromatography, or the like.

According to the invention, the cellulase variant may typically be added as a component of a detergent composition. As such, it may be included in the detergent composition in the form of a non-dusting granulate, a liquid, in particular a stabilized liquid, or a protected enzyme. Non-dusting granulates may be produced, e.g., as disclosed in U.S. Pat No. 4,106,991 and 4,661,452 (both to Novo Industri A/S) and may optionally be coated by methods known in the art. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238,216. The detergent composition may further include one or more other enzymes, such as a protease, lipase, peroxidase, oxidase or amylase, conventionally included in detergent additives.

The detergent composition of the invention may be in any convenient form, e.g. as powder, granules or liquid. A liquid detergent may be aqueous, typically containing up to 90% water and 0–20% organic solvent.

The detergent composition comprises a surfactant which may be anionic, non-ionic, cationic, amphoteric or a mixture of these types. The detergent will usually contain 0–50% anionic surfactant such as linear alkyl benzene sulphonate (LAS), alpha-olefin sulphonate (AOS), alkyl sulphate (AS), alcohol ethoxy sulphate (AES) or soap. It may also contain 0–40% non-ionic surfactant such as nonyl phenol ethoxylate or alcohol ethoxylate. Furthermore, it may contain a polyhydroxy fatty acid amide surfactant (e.g. as described in WO 92/06154).

The detergent composition may additionally comprise one or more other enzymes, such as an amylase, lipase, peroxidase, oxidase, esterase, cellulase, endoglucanase type II or protease.

The pH (measured in aqueous detergent solution) will usually be neutral or alkaline, e.g. 7–11. The detergent may contain 1–40% of a detergent builder such as zeolite, phosphate, phosphonate, citrate, NTA, EDTA or DTPA, alkenyl succinic anhydride, or silicate, or it may be unbuilt (i.e. essentially free of a detergent builder). It may also contain other conventional detergent ingredients, e.g. fabric conditioners, foam boosters, bleaching agents, e.g. perborate, percarbonate, tetraacetyl ethylene diamine (TAED) or nonanoyloxybenzene sulphonate (NOBS), anti-corrosion agents, soil-suspending agents, sequestering agents, anti-soil redeposition agents, stabilizing agents for the enzyme(s), foam depressors, dyes, bactericides, optical brighteners or perfumes.

Particular forms of detergent composition within the scope of the invention include:

a) A detergent composition formulated as a detergent powder containing phosphate builder, anionic surfactant, nonionic surfactant, silicate, alkali to adjust to desired pH in use, and neutral inorganic salt.

b) A detergent composition formulated as a detergent powder containing zeolite builder, anionic surfactant, nonionic surfactant, acrylic or equivalent polymer, silicate, alkali to adjust to desired pH in use, and neutral inorganic salt.

c) A detergent composition formulated as an aqueous detergent liquid comprising anionic surfactant, nonionic surfactant, humectant, organic acid, caustic alkali, with a pH in use adjusted to a value between 7 and 11.

d) A detergent composition formulated as a nonaqueous detergent liquid comprising a liquid nonionic surfactant consisting essentially of linear alkoxylated primary alcohol, phosphate builder, caustic alkali, with a pH in use adjusted to a value between about 7 and 11.

e) A detergent composition formulated as a detergent powder in the form of a granulate having a bulk density of at least 600 g/l, containing anionic surfactant and nonionic surfactant, low or substantially zero neutral inorganic salt, phosphate builder, and sodium silicate.

f) A detergent composition formulated as a detergent powder in the form of a granulate having a bulk density of at least 600 g/l. containing anionic surfactant and nonionic surfactant, low or substantially zero neutral inorganic salt, zeolite builder, and sodium silicate.

g) A detergent composition formulated as a detergent powder containing anionic surfactant, nonionic surfactant, acrylic polymer, fatty acid soap, sodium carbonate, sodium sulphate, clay particles, and sodium silicate.

h) A liquid compact detergent containing 5–65% by weight of surfactant, 0–50% by weight of builder and 0–30% by weight of electrolyte.

Apart from these ingredients, the detergent compositions a)–h) include a cellulase variant of the invention and optionally one or more other enzymes, as indicated above.

It is at present contemplated that, in the detergent composition of the invention, the cellulase variant may be added in an amount corresponding to 0.001–100 mg enzyme per liter of wash liquor.

The following examples illustrate the invention and should not be construed in any way as limiting the scope of the present invention:

EXAMPLE 1

Effect of variations in the linking region on residual activity

The residual activity of the cellulase variants after storage in liquid detergent containing protease enzymes has been evaluated with two different assays.

The S-CEVU assay quantifies the amount of catalytic activity present in the sample by measuring the ability of the sample to reduce the viscosity of a solution of carboxymethylcellulose (CMC). This activity is only related to the enzyme core and is unaffected by the presence or absence of the linking region and the CBD region.

The S-CEVU assay is carried out at 40° C., pH 7.5 using an relative enzyme standard for reducing the viscosity of the substrate (CMC). The method is available from the Applicant as No. AF-302/2GB upon request.

The Dyed Avicel Assay (DAA) quantifies the amount of cellulase able to attach to insoluble cellulose and release dye bound to the surface of the cellulosic powder. Cellulases without the linking region and the CBD region exhibit low activity on this substrate and the assay can therefore be used to monitor the proteolytic degradation of intact cellulases to enzyme core.

Since the washing performance of cellulases without the linking region and the CBD region is lower than for intact enzymes, the DAA correlates to some degree with the washing performance of cellulases stored in detergent containing protease enzyme(s).

The following cellulase variants according to the present invention were tested for residual activity:

Variant I: V221S+N222S+Q223T

Variant II: V240P+Q241P

The *H. insolens* 43 kD endoglucanase described in W091/17243 was used as the reference (parent) cellulase.

DYED AVICEL ASSAY, (DAA).

The enzymatic reaction of a cellulase with a cellulose powder dyed with Remazol Brilliant Blue releases an amount of dye related to the activity of the cellulase.

| Reaction conditions: | |
|---|---|
| pH | 7.50 |
| Temperature | 40° C. |

-continued

| Reaction conditions: | |
|---|---|
| Substrate | Dyed microcrystalline cellulose |
| Buffer | 0.1M Phosphate Buffer pH 7.5 with 1 g/l nonionic tenside (Berol 160). |
| Time | 60 iuinutes |
| Sample concentration | 0.5–15 S-CEVU/ml |

Preparation of dyed cellulose 50 g of Sigmacell type 20 cellulose powder was added to 500 ml of deionized water in a 2000 ml glass beaker and stirred with a magnetic stirrer. 4 g of Remazol Brilliant Blue R 19 Dye (C.I. 61200 Reactive Blue 19) was dissolved in 350 ml of deionized water. The dye solution was added to the suspension of Sigmacell and heated to about 55° C. The mixture was stirred for 30 minutes while 100 g of anhydrous sodium sulphate was slowly added.

20 g of trisodium phosphate dodecahydrate was dissolved in 200 ml of deionized water. pH of the Sigmacell/dye solution was adjusted to 11.5 by adding about 150 ml of the trisodium phosphate solution.

The mixture was stirred for 60 minutes at 55° C.

The mixture was vacuum filtered by means of a 1000 ml Buüchner funnel and Whatman No.54 filter paper. The filter cake was washed repeatedly with deionized water at 70° C.–80° C. until the optical density at: 590 nm ($OD_{590}$) of the filtrate (the waste water) was below 0.03.

The filter cake was rinsed with 100 ml of 50% ethanol resulting in further removal of blue colour and subsequent with 100 ml of 96% ethanol.

The cellulose was removed from the funnel and left to dry (in clean bench).

| ASSAY REAGENTS | |
|---|---|
| 0.1M Phosphate Buffer | |
| $NaH_2PO_4O_2H_2O$ (Merck 6345.1000) | 15.6 g |
| Deionised water | add 800 ml |
| Berol 160 (AEO) | 1.0 g |
| NaOH, 4N | adjust pH to 7.5 |
| Deionised water | fill up to 1000 ml |
| pH is checked 7.5 +/– 0.03 | |
| Nonionic stop reagent | |
| Tri-Sodium Phosphate (Merck 6578) | 19 g |
| Deionised water | add 950 ml |
| Berol 160 | 20 g |
| Stir until completely clear. | |
| Deionised water fill up to 1000 ml | |
| Dyed Cellulose substrate | |
| Must be prepared fresh every day. The dry powder is weighed out and a 10% (w/w) solution in 0.1M phosphate buffer (as described) is prepared. Stir for at least 30 minutes before starting assay. | |
| Enzyme sample diluted in 0.1M Buffer | |
| Samples are diluted in 0.1M phosphate buffer to a concentration of eg. 4, 8, 12, 16 S-CEVU/ml | |

Enzyme standard

An appropriate enzyme standard, or the reference non-stored sample, was diluted in 0.1M phosphate buffer to produce a standard curve.

Concentrations of the standard eg. 0, ½, 1, 2, 4, 8, 12, 16 S-CEVU/ml

APPARATUS

Water bath at 40° C.
Spectrophotometer (590 nm)
Variomag Telesystem HP 60 P, submersible magnetic stirrer plate, (60 points).
Variomag Test Tube Rack HP 60, for 16 mm test tubes. Test tubes, 16 mm $\phi$
Magnetic stirring rods, 3×8 mm.
Filter paper $\phi$ 9 cm, Munktell 1F.
Filtrating funnels
Finnpipette 1–5 ml
Test tubes and rack for collection of the filtrate
Magnetic stirrer plate and magnet for substrate suspension.

METHOD

The temperature of the water bath must be 40° C. 2 ml of sample or standard solution were measured into test tubes placed in rack. When all tubes were ready, rack was placed in the water bath.

Figure 8:
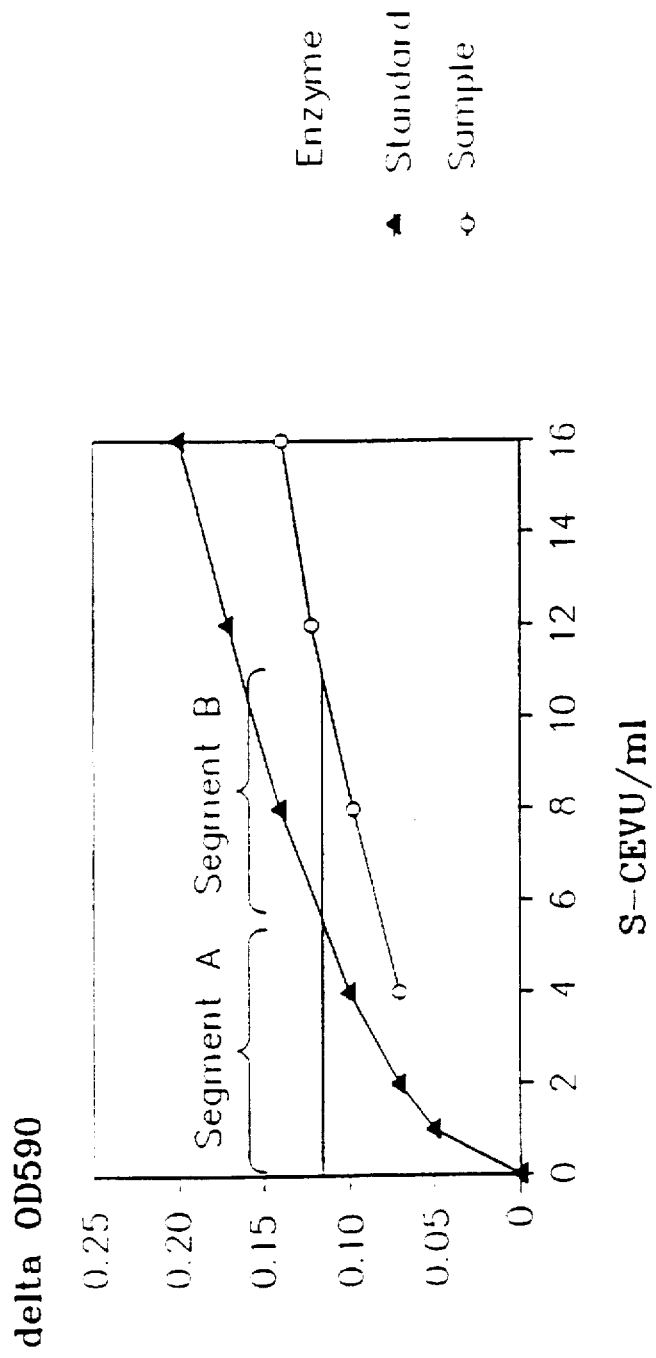
FIG. 8 shows a standard curve and sample response in Dyed Avicel Assay.

A magnetic stirring rod was added to all tubes, the stirrer plate was started at 600 rpm. With 10 seconds interval, 2 ml of Dyed Cellulose Substrate was added with constant stirring during the pipetting. After 60 min reaction time 2 ml Nonionic stop reagent was added to each tube. The well mixed sample at 40° C. was poured onto a paper filter in a filtrating funnel, and the clear filtrate was collected. The filtration must be repeated, if the filtrate is unclear. The absorbance at 590 nm of the filtrate was measured. The absorbance of the standard without enzyme, 0 S-CEVU/ml, was subtracted from the absorbance of the samples and other standards. The resulting delta absorbance at 590 nm was plotted against the enzyme activity in the sample solution measured in S-CEVU/ml. The dose-response curve is not linear, (FIG. 8), and the activity of the sample relative to the standard, (or of a stored sample relative to a non-stored sample) can be calculated as shown.

EXPERIMENTAL, storage stability

2475 S-CEVU of a highly purified cellulase was freeze dried. 1.65 g liquid detergent was added and stirred until cellulase was dissolved. 0.165 KNPU(S) Savinase® protease was added and mixed thoroughly. 100 µl detergent with enzymes was pipetted into (max) seven 1 ml Nunc-tubes. One of the tubes was immediately put in the deep-freezer (−18° C.) for reference. The remaining (6) tubes were incubated at 25° C. and 35° C., for 1,2 or 5 days. After incubation, the samples were diluted to working concentration, and the residual activity of the stored samples relative to the non-stored reference was determined in the Dyed Avicel Assay. Residual activity of the samples relative to the reference with respect to the activity in S-CEVU/g was also determined.

Figure 9:
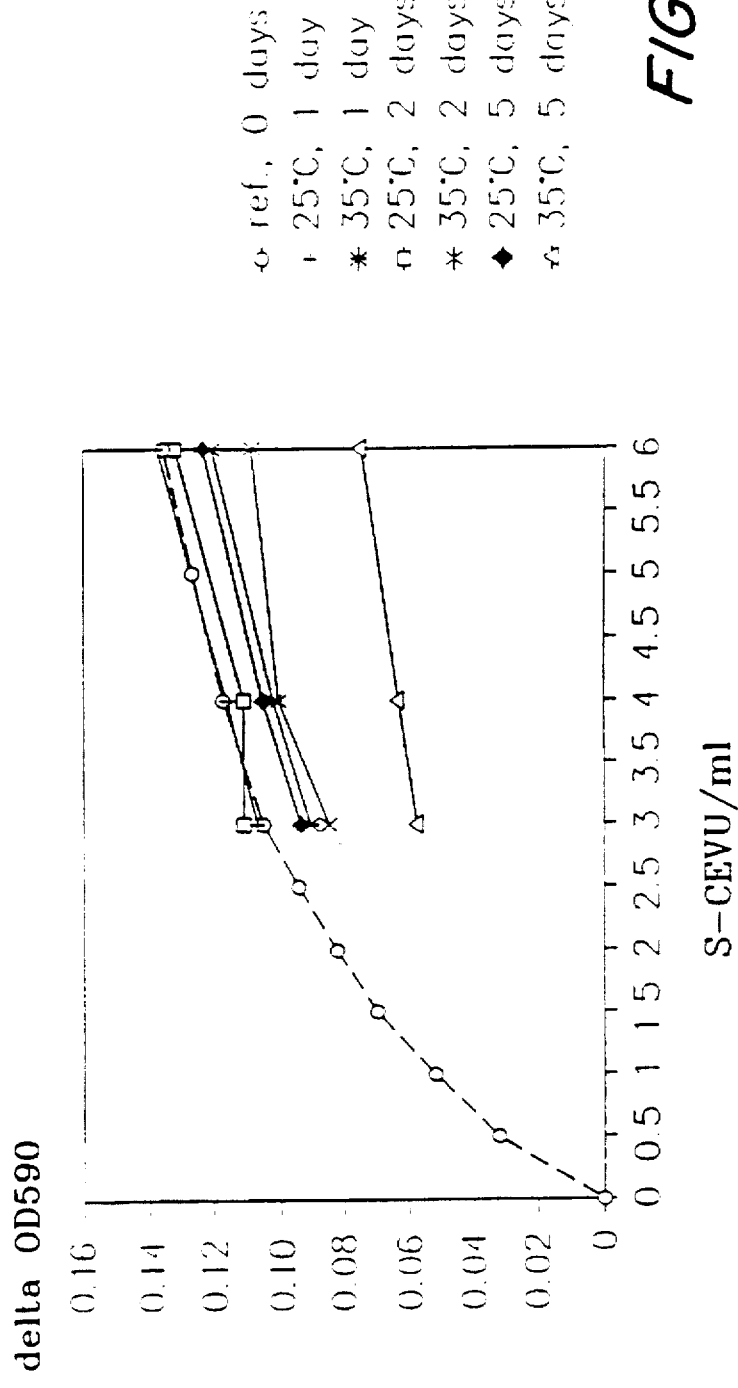
FIG. 9 shows the storage stability of a 43 kD cellulase variant (V221S+N222S+Q223T) in liquid detergent.

FIG. 9 shows an example of curves from Dyed Avicel Assay with cellulase variant I.

EXAMPLE 2

Cellulase adsorption on amorphous cellulose

Avicel® (Asahi Chemical Co. Ltd., Japan), amorphisized by swelling in 85% phosphoric acid was used as test adsorbent, see example 5 below for further details.

The test adsorbent was stored as suspension in distilled water, the content of dry cellulose (typically 15 g/l) being determined by drying and weighting an aliquot in a separate experiment. The adsorbent was dosed by volume (0–0.5 ml) into plastic tubes, that can be sealed, to receive content of cellulose dry mass in the range of 0–8 mg. The volume was adjusted to 0.5 ml by distilled water. Ariel Color which is a commercial compact powder detergent was pretreated in order to inactivate enzymes present in the powder detergent by incubating the detergent in a microwave oven for 8 min. at 85° C. 0.3 ml of the pretreated Ariel Color solution (21.67 g/l) in 1M Gly-NaOH buffer pH 10 was added to each tube, followed by an aliquot of 0.2 ml of enzyme (5 IU/ml) to provide the initial EG activity in the mixture of about 1 IU/ml.

The suspension was shaken for 60 min on a Swelab Instrument 440 mixer at 200°, 1 sec$^{-1}$ and the substrate with enzyme adsorbed was sedimented by centrifuging at 2500 g, 20° for 5 min.

The supernatant was assayed for the unbound endoglucanase activity using a conventional technique such as Red CMC assay (Tikhomirov D. F. et al., *Biotechnologia* (Moscow), translated into English by Plenum Press, 1989, Vol. 5, No. 4, p. 518–524).

Enzyme aliquots of 100 µl were added to 1 ml of 1% Red CMC substrate (Fermentas Co., Vilnius, Lithuania), pH 7.5 (0.05M Tris buffer), in narrow glass tubes, the mixture being transferred to a water thermostat, 40°, for 40 min. One more tube was added to the thermostat with buffer instead of enzyme aliquot as blank. The enzymatic reaction was stopped by addition of 1 ml of 80% ethanol containing 0.1M $CaCl_2$ with subsequent vigorous shaking. The unhydrolysed substrate was separated by centrifuging the same tubes at 4000 g for 10 min and the supernatant absorbance at 490 nm was measured against water.

The degree of adsorption was plotted in terms of the $A_0/A_{super}$ ratio versus the adsorbent concentration—a linearisation method which gives a straight line in case of a single endoglucanase isoform, homogeneous according to adsorption properties (Klyosov A. A. et al., *Bioorgan. Chem.* (Moscow), translated into English by Plenum Press, 1982, Vol. 8, No. 5, p. 643–651). The constant of distribution, $K_d = A_{bound}/(A_{super}[S])$, may be determined from this plot as the slope of the line.

RESULTS

| | Residual Activity, % DAA | | | | | | Residual Activity, % S-CEVU | | | | | |
|---|---|---|---|---|---|---|---|---|---|---|---|---|
| | 25° C., days | | | 35° C., days | | | 25° C., days | | | 35° C., days | | |
| Enzyme | 1d | 2d | 5d | 1d | 2d | 5d | 1d | 2d | 5d | 1d | 2d | 5d |
| Carezyme | 86 | 81 | 63 | 70 | 52 | 33 | 102 | 99 | 93 | 102 | 92 | 82 |
| Variant I | 105 | 94 | 83 | 78 | 72 | 34 | 98 | 96 | 98 | 97 | 97 | 82 |
| Variant II | 100 | 100 | 81 | 76 | 68 | 44 | 99 | 97 | 88 | 89 | 81 | 76 |

The following $K_d$ values were obtained in Ariel Color:

| | |
|---|---|
| Carezyme | 0.6 l/g |
| Y280F | 2.9 l/g |
| R252F | 4.3 l/g |
| Y280F + R252F | 3.3 l/g |

EXAMPLE 3

Washing trials
A. Conditions
Apparatus: Terg-o-tometer
Liquid volume: 150 ml
agitation: 100 movements/min
washing time: 30 min
rinse time: 5 min in tap water
washing temp: 40°
textile: 2 swatches 100% aged black cotton 5×6 cm
Drying: Line drying
repetitions: 3
Pretreatment of commercial detergents: Incubation in a microwave oven for 8 min at 85° C.
Evaluation: The members of the panel are asked to give relative ranking of the surfaces within an experiment in respect to color clarity and level of fuzz. The higher number the better performance.

1. Carezyme versus Y280F

Detergent: Commercial European Compact Color Powder Granulate, 6.5 g/l, pH 10.2.

Water hardness: 3 mM Ca++

| | | Average panel score (score 1–6) |
|---|---|---|
| No enzyme | | 1.0 |
| Carezyme | 500 S-CEVU/1 | 3.4 |
| Y280F | 500 S-CEVU/1 | 4.3 |

The data show that the variant have improved performance under the conditions tested.

2. Carezyme versus
   1) V221S-N222S-Q223T,
   2) Y8F,
   3) Del(S219-T235)
   Detergent: Commercial US Heavy Duty Compact Powder Granulate, 1 g/l, pH 10.
   Water hardness: 1 mM Ca++

| | | Average panel score (score 1–11) |
|---|---|---|
| No enzyme | | 1.0 |
| Carezyme | 250 S-CEVU/1 | 4.0 |
| Carezyme | 500 S-CEVU/1 | 6.5 |
| Carezyme | 1000 S-CEVU/1 | 9.0 |
| 1) | 500 S-CEVU/1 | 10.0 |
| 2) | 500 S-CEVU/1 | 8.0 |
| 3) | 500 S-CEVU/1 | 11.0 |

The data show that all three variants have improved performance under the conditions tested.

B. Conditions
Apparatus: Terg-o-tometer
Liquid volume: 800 ml
washing time: 12 min
rinse time: 4 min in tap water
washing temp: 35°
textile: 2 swatches 100% aged black cotton 10×15 cm
Drying: Tumble drying
repetitions: 11
Pretreatment of commercial detergents: Incubation in a microwave oven for 8 min at 85° C.
Evaluation: The members of the panel are asked to grade the enzyme treated surface versus no enzyme in respect to visual appearance (color clarity and fuzz) according to a determined scale. Rank:
0=no benefit
1=recognizable benefit
2=easy recognizable benefit
3=Large benefit
4=Very large benefit
5=new textile 1. Carezyme versus A162P Detergent: Commercial US Compact Color Powder Granulate, 1 g/l, pH 8.1.

Water hardness: 1 mM Ca++ & 0.35 mM Mg

| | | Average panel score |
|---|---|---|
| No enzyme | | 0 |
| Carezyme | 15 S-CEVU/1 | 1.5 |
| Carezyme | 30 S-CEVU/1 | 2.0 |
| A162P | 15 S-CEVU/1 | 1.8 |
| A162P | 30 S-CEVU/1 | 2.7 |

C. Conditions
Apparatus: Terg-o-tometer
Liquid volume: 800 ml
agitation: 100 movements/min
washing time: 30 min
rinse time: 10 min in tap water
washing temp: 40°
textile: 2 swatches 100% aged black cotton 10×15 cm
Drying: Tumble drying repetitions: 4
Pretreatment of commercial detergents: Incubation in a microwave oven for 8 min at 85° C.
Evaluation: The members of the panel are asked to grade the enzyme treated surface versus no enzyme in respect to visual appearance (color clarity and fuzz) according to a determined scale. Rank
0=no benefit
1=recognizable benefit
2=easy recognizable benefit
3=Large benefit
4=Very large benefit
5=new textile 1. Carezyme versus W62E Detergent: Commercial European Compact Powder Granulate, 6.5 g/l, pH 10.2.

Water hardness: 3 mM Ca++

| | | Average panel score |
|---|---|---|
| No enzyme | | 0 |
| Carezyme | 50 S-CEVU/1 | 1.0 |
| Carezyme | 80 S-CEVU/1 | 1.3 |
| Carezyme | 120 S-CEVU/1 | 1.8 |
| Carezyme | 150 S-CEVU/1 | 2.0 |
| W62E | 100 S-CEVU/1 | 1.9 |

EXAMPLE 4

Peroxidase stabilised 43 kD cellulase variant

The peroxidase system (POD system) used for Dye Transfer Inhibition (DTI), comprising a coprinus cinereus peroxidase (CiP, obtained according to EP Patent Application 179,486), hydrogen peroxide, and p-hydroxy benzene sulphonate (pHBS) as peroxidase enhancing agent was simulated in a Britton-Robinson buffer, pH 8.5:

[pHBS]: 50 µM, [H$_2$O$_2$]: 200 µM, [CiP]: 2 PODU/ml, [cellulase]: 1.4 ECU/ml, 10 mM Britton-Robinson buffer, pH 8.5.

The 43 kD cellulase and the cellulase variant Y147S were incubated with the POD system for 10 min at 35 °C. Samples were withdrawn and diluted 5 times with ice-cold 0.1M sodium phosphate, pH 7.0. The residual activities of the cellulases were measured by the CMCU method using the ferricyanide detection principle.

The results are presented in the table below which shows that the substitution Y147S leads to a cellulase variant which is stable towards the POD system.

| Cellulases | Residual activity after POD treatment (%) |
| --- | --- |
| 43 kD cellulase | 10 |
| Variant Y147S | 85 |

EXAMPLE 5

Determination of alkaline cellulase activity on amorphous cellulose

Method

Substrate preparation: 20 gram acid-swollen AVICEL® stock solution (see below for a preparation which can be stored for one month) was centrifuged for 20 min. at 5000 rpm., the supernatant was poured off, and the sediment was resuspended in 30 ml of buffer. Then centrifuged for 20 min. at 5000 rpm, the supernatant was poured off, and the sediment was resuspended in buffer to a total of 30 g. This corresponds to a substrate concentration of 10 g AVICEL/liter.

Buffer: 0.1M Barbital at pH 8.5 or 0.1M Glycine at pH 10.0

Enzyme solution

The enzymes were diluted to an activity of 0.5 S-CEVU/ml at pH 8.5 or 0.75 S-CEVU/ml at pH 10.0.

Reagents

2% NaOH, PHBAH-reagent: 1.5 g of p-hydroxy benzoic acid hydrazide and 5.0 g sodium tartrate was dissolved in 100 ml of 2% NaOH.

The substrate, the buffer and the enzyme solution were mixed as follows:

| Substrate µl | Buffer µl | Enzyme sol. µl | Subst. conc. (final) g/l |
| --- | --- | --- | --- |
| 50 | 1950 | 500 | 0.20 |
| 125 | 1875 | 500 | 0.50 |
| 250 | 1750 | 500 | 1.00 |
| 500 | 1500 | 500 | 2.00 |
| 750 | 1250 | 500 | 3.00 |
| 1000 | 1000 | 500 | 4.00 |

The subtrate/buffer solution was preheated for 5 min at 40° C. the enzyme solution was added and the solution was whirlmixed for 5 sec., followed by incubation for 20 min. at 40° C.

The reaction was stopped by adding 500 µl. 2% NaOH solution, followed by whirlmixing for 5 sec.

The samples were centrifuged for 20 min. at 5000 rpm. 1000 µl of supernatant was transferred from the test tubes to test tubes, and 500 µl PHBAH-reagent was added, followed by boiling for 10 min.

The test tubes were cooled in ice water.

The absorbance of the samples were measured on a spectro-photometer at 410 nm.

standard glucose curve

A stock solution containing 300 mg/l was diluted to 5, 10, 15 and 25 mg/l.

1000 µl of the diluted standards were mixed with 500 µl of PHBAH-reagent, and were treated as the other samples, see above.

Determination of activity

The release of reducing glucose equivalent was calculated using the standard curve.

The enzyme concentration was calculated using the molar absorbance of 61300 (ε) for the 43 kD endoglucanase. The $K_m$, $V_{max}$ and $K_{cat}$ was calculated from a Lineweaver-Burk plot using different substrate concentrations.

The molar absorbance of the cellulase variants having substituted tyrosines and tryptophanes was adjusted accordingly using a absorbance value for tryptophane of 5690(ε) and for tyrosine of 1280(ε) and cystein 120(ε).

The extinction coefficients (ε) are disclosed in Gill, S. C. and Hippel, P. H.: Calculation of protein extinction coefficients from amino acid sequence data; Analytical Biochemistry vol 182, (319–326), (1989).

Each of the tested cellulase variants was purified to high homogeneity giving a single band in SDS-PAGE analysis (the ratio $A_{280}/A_{260}$ was checked as being above 1.5).

Preparation of Acid swollen cellulose

Materials 5 g Avicel®. (Art. 2331 Merck)

150 ml 85% Ortho-phosphoric-acid. (Art. 573 Merck)

400 ml Acetone. (Art. 14 Merck)

1.3 l Deionized water (Milli Q)

1 l glass beaker 1 l glass filter funnel 2 l suction flask

Ultra Turrax Homogenizer

Procedure

The Acetone and the phosphoric-acid was cooled on ice. The 5 g. Avicel® was moistened with water, then 150 ml of ice cold 85% Ortho-phosphoric-acid was added, and the mixture was placed on ice bath with weak stirring for 1 h. 100 ml of ice cold acetone was added with stirring, followed by transfer of the mixture to a glass filter funnel, followed by washing with 3×100 ml ice cold acetone and dry suction after each washing.

The filter cake was washed with 2×500 ml water and sucked as dry as possible after each wash.

The filter cake was resuspended to a total volume of 300 ml and blended to homogeneity (using the Ultra Turrax Homogenizer).

The resulting product was stored in a refrigerator.

The following results was obtained with 43 kD cellulase and the variants A162P and W62E, respectively:

|        | Kcat at pH 8,5 per sec. | Kcat at pH 10 per sec |
|--------|-------------------------|------------------------|
| 43 kD  | 57                      | 25                     |
| A162P  | 64                      | 36                     |
| W62E   | 41                      | 31                     |

As can be seen from the table, both substitution have enhance catalytic activity on the substrate amorphous Avicel under alkaline condition (pH 10.0).

EXAMPLE 6

LAS inhibition of cellulase

The cellulase was incubated with different concentrations of LAS (linear alkyl benzene sulphonate; Nansa 1169/P) for 10 min at 40° C.

The residual activity was determined using the CMCU method described below.

LAS was diluted in 0.1M phosphate buffer pH 7.5.

The following concentrations were used:

500 ppm, 250 ppm, 100 ppm, 50 ppm, 25 ppm, and 10 ppm on no LAS.

The cellulase was diluted in the different LAS buffers to 0.2 S-CEVU//ml final concentration in a total volume of 10 ml and incubated for 10 min in a temperature controlled water bath.

Then the residual activity was determined in duplicate using the CMCU substrate and measuring reducing sugars. The two samples of 0.5 ml solution were mixed with 1.5 ml 1% CMC solution (Hercules 7L) prepared in the same phosphate buffer, incubation for 20 min at 40° C., and then stopped with PHBAH, sodium tartrate in 2% NaOH.

The similar blank sample of 0.5 ml was added to the CMC solution after addition of stop reagent.

The samples was cooked for 10 min and the absorbance was measured at 410 nm.

The activity was measured after subtraction of the blank. The activity with no LAS was 100%.

Figure 10:
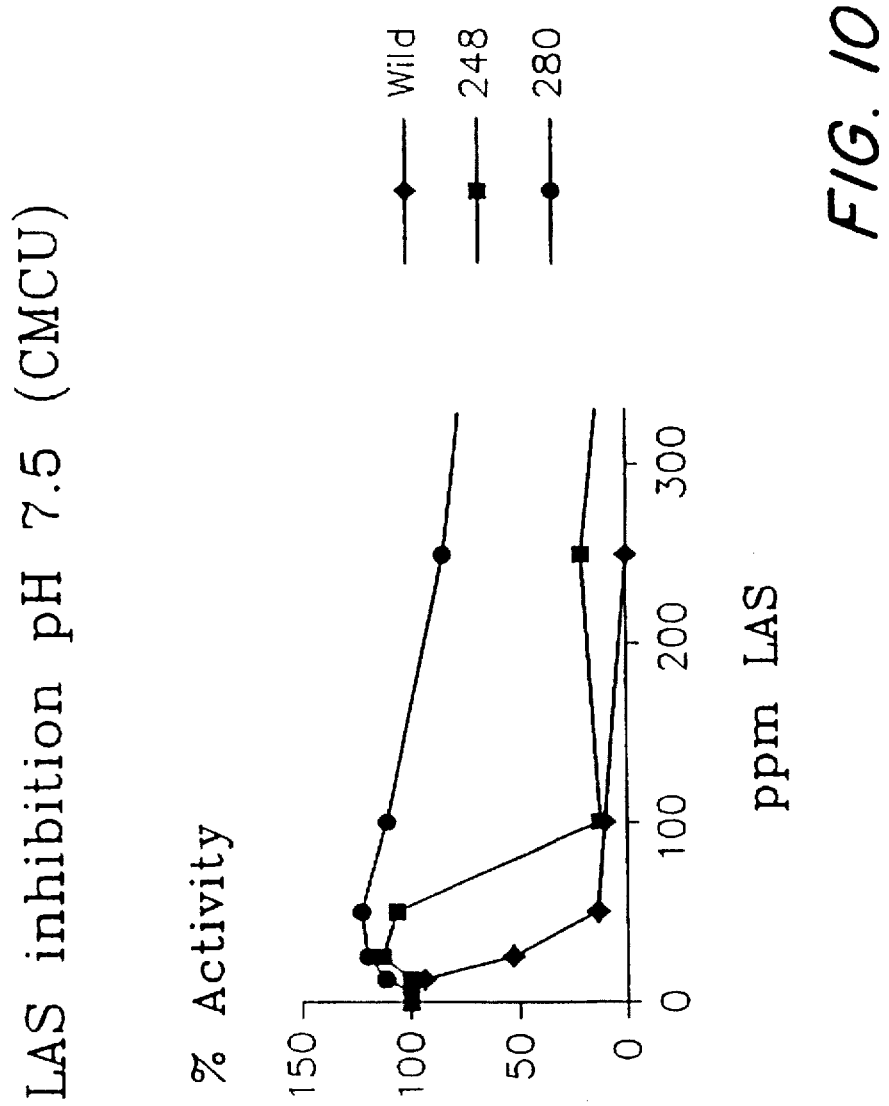
FIG. 10 shows the LAS (linear alkyl sulphonate) inhibition at pH 7.5.

In FIG. 10 is shown the residual activity of the 43 kD cellulase and the cellulase variants A162P and R158E, respectively. The 43 kD cellulase is denoted "Wild", the A162P variant is denoted "248", and the R158E variant is denoted "280".

As can be seen from the figure the substitution of A162P or R158E enhance the stability of the cellulase against LAS (anionic surfactant).

---

We claim:

1. A cellulase having the amino acid sequence of SEQ ID NO:8, 9, or 10, wherein relative to SEQ ID NO:10

(a) one or more amino acid residues are substituted by a different amino acid residue, at one or more of positions 252 or 280;

(b) one or more amino acid residues are substituted by a different amino acid residue at one or more of positions 221, 222, 223, 240, and 241, or amino acids at positions 219–235 are deleted; and (c) one or more amino acid residues are substituted by a different amino acid residue, said substitutions selected from the group consisting of one or more amino acid residues at positions 8, 62, 147, 158, or 162, wherein the variant exhibits increased alkaline activity relative to the non-substituted cellulase.

2. The variant of claim 1, comprising one or more of the amino acid substitutions of R252L, R252Q, R252H, Y280W, or Y280F (SEQ ID NO:10), or A322L, A252Q A252H Y280W or Y280F (SEQ ID NO:9).

3. The variant of claim 1, comprising one or more of the amino acid substitutions of V221S, V221T, V221P, N222S, N222T, N222P, Q223S, Q223T, Q223P, V240S, V240T, V240P, Q241S, Q241T, and Q241P (SEQ ID NO:10), or P224S, P224T, S225T, S225P, S226T, S226P, T243S, T243P, K244S, K244T, and K244P (SEQ ID NO:9).

4. The variant of claim 3 comprising one or more of the amino acid residue substitutions of V221S, N222S, and Q223T (SEQ ID NO:10) or P224S, S226T (SEQ ID NO:9).

5. The variant of claim 3, further comprising one or more substitutions V240P and Q241P (SEQ ID NO:10) or T243P and K244P (SEQ ID NO:9).

6. The variant of claim 1, wherein the substitutions are selected from the group consisting of Y8F, W62F, W62E, Y147F, Y147H, Y147S, Y147Q, Y147N, Y147E, and Y147D (SEQ ID NO:10) or Y9F, W64F, W64E, Y150F, Y150H, Y150S, Y150Q, Y150N, Y150E, and Y150D (SEQ ID NO:9) or Y15F, F69E, Y163F, Y163H, Y163S, Y163Q, Y163N, Y163E, and Y163D (SEQ ID NO:8).

7. A detergent composition comprising the cellulase variant of claim 1 and a surfactant.

8. The variant of claim 1, wherein the parent cellulase is a H. insolens 43 kD endoglucanase (SEQ ID NO:10).

* * * * *

UNITED STATES PATENT AND TRADEMARK OFFICE
CERTIFICATE OF CORRECTION

PATENT NO.    : 5,792,641
DATED         : August 11, 1998
INVENTOR(S)   : Schulein et al.

It is certified that error appears in the above-identified patent and that said Letters Patent is hereby corrected as shown below:

Columns 31 and 32,
Delete line beginning with amino acid 65, and replace with the following:
Asp Lys Ile Pro Phe Ala Val Ser Pro Thr Leu Ala Tyr Gly Tyr Ala
65                      70                      75                      80

Column 33,
Delete line, "(A)Length: 357 amino acids" and replace with -- (A)Length: 358 amino acids --

Columns 35 and 36,
Delete lines beginning with amino acid 225 and ending with amino acid 256, and replace with the following:
Ser Ser Ala Lys Lys Thr Thr Ser Ala Ala Ala Ala Ala Gln Pro Gln
225                     230                     235                     240
Lys Thr Lys Asp Ser Ala Pro Val Val Gln Lys Ser Ser Thr Lys Pro
                        245                     250                     255

Delete lines beginning with amino acid 321 and ending with amino acid 357, and replace with the following:
Ala Tyr Tyr Gln Cys Gly Gly Ser Lys Ser Ala Tyr Pro Asn Gly Asn
                        325                     330                     335
Leu Ala Cys Ala Thr Gly Ser Lys Cys Val Lys Gln Asn Glu Tyr Tyr
                        340                     345                     350
Ser Gln Cys Val Pro Asn
        355

UNITED STATES PATENT AND TRADEMARK OFFICE
CERTIFICATE OF CORRECTION

PATENT NO.   : 5,792,641
DATED        : August 11, 1998
INVENTOR(S)  : Schulein et al.

It is certified that error appears in the above-identified patent and that said Letters Patent is hereby corrected as shown below:

Column 37,
Line 40, delete "A252O" and insert -- A252Q, --
Line 41, delete "A252H Y280W or" and insert -- A252H, Y280W, or --

Signed and Sealed this

Fifth Day of August, 2003

JAMES E. ROGAN
*Director of the United States Patent and Trademark Office*